(12) United States Patent
Sexton et al.

(10) Patent No.: US 9,538,775 B2
(45) Date of Patent: *Jan. 10, 2017

(54) SUSTAINED RELEASE OF NUTRIENTS IN VIVO

(71) Applicant: NEW WORLD PHARMACEUTICALS, LLC, Rumson, NJ (US)

(72) Inventors: Frederick Sexton, Rumson, NJ (US); Sitaraman Krishnan, Potsdam, NY (US); Venkat Kalyan Vendra, Potsdam, NY (US)

(73) Assignee: New World Pharmaceuticals, LLC, Charleston, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/027,965

(22) Filed: Sep. 16, 2013

(65) Prior Publication Data
US 2014/0242212 A1 Aug. 28, 2014

Related U.S. Application Data

(63) Continuation of application No. 12/337,022, filed on Dec. 17, 2008, now Pat. No. 8,563,066.
(Continued)

(51) Int. Cl.
*A23L 1/29* (2006.01)
*A23L 1/00* (2006.01)
(Continued)

(52) U.S. Cl.
CPC ............... *A23L 1/0029* (2013.01); *A23G 4/06* (2013.01); *A23L 1/052* (2013.01); *A23L 1/0545* (2013.01);
(Continued)

(58) Field of Classification Search
CPC ...... A23L 1/3084; A23L 1/0029; A23L 1/296; A23V 2250/51086; A23V 2250/51088
(Continued)

(56) References Cited

U.S. PATENT DOCUMENTS 4,857,331 A    8/1989   Shaw et al.
5,484,610 A    1/1996   Bae
(Continued)

FOREIGN PATENT DOCUMENTS

CN    101450996 A    6/2009
EP    1304044 A2     4/2003
(Continued)

OTHER PUBLICATIONS

Akiyoshi, K.; Deguchi, S.; Tajima, H.; Nishikawa, T.; Sunamota, J. Self-assembly of hydrophobized polysaccharide: Structure of hydrogel nanoparticle and complexation with organic compounds. Proc. Japan Acad. 1995, 71, 15-19.
(Continued)

*Primary Examiner* — Helen F Heggestad
(74) *Attorney, Agent, or Firm* — Frommer Lawrence & Haug LLP

(57) ABSTRACT

Nutritional compositions delivered in vivo in a time controlled manner sustainable over long periods of time, provide enhancing athletic performance, increased hand/eye coordination and concentration on the task at hand.

19 Claims, 8 Drawing Sheets

Carboxymethyl cellulose

Alginic acid

Hyaluronic acid

Related U.S. Application Data

(60) Provisional application No. 61/014,251, filed on Dec. 17, 2007.

(51) Int. Cl.

| | | |
|---|---|---|
| *A23G 4/06* | (2006.01) | |
| *A23L 1/052* | (2006.01) | |
| *A23L 1/054* | (2006.01) | |
| *A23L 1/09* | (2006.01) | |
| *A23L 1/302* | (2006.01) | |
| *A23L 1/304* | (2006.01) | |
| *A23L 1/305* | (2006.01) | |
| *A23L 1/308* | (2006.01) | |
| *A23L 2/52* | (2006.01) | |

(52) U.S. Cl.
 CPC ............... *A23L 1/09* (2013.01); *A23L 1/293* (2013.01); *A23L 1/296* (2013.01); *A23L 1/302* (2013.01); *A23L 1/304* (2013.01); *A23L 1/3051* (2013.01); *A23L 1/3082* (2013.01); *A23L 1/3084* (2013.01); *A23L 2/52* (2013.01); *A23V 2002/00* (2013.01)

(58) Field of Classification Search
 USPC ............... 426/2, 72, 73, 74, 573, 590, 648, 656,426/658, 601
 See application file for complete search history.

(56) References Cited

U.S. PATENT DOCUMENTS

| | | |
|---|---|---|
| 5,536,156 A | 7/1996 | Fox et al. |
| 5,795,606 A | 8/1998 | Lapre et al. |
| 5,807,575 A | 9/1998 | Dumoulin et al. |
| 5,840,338 A | 11/1998 | Roos et al. |
| 6,018,033 A | 1/2000 | Chen et al. |
| 6,224,893 B1 | 5/2001 | Langer et al. |
| 6,387,987 B2 | 5/2002 | Sakamoto et al. |
| 6,426,086 B1 | 7/2002 | Papahadjopoulos et al. |
| 6,429,198 B1 | 8/2002 | St. Cyr et al. |
| 6,602,524 B2 | 8/2003 | Batich et al. |
| 6,677,386 B1 | 1/2004 | Giezen et al. |
| 7,329,419 B2* | 2/2008 | Yatcilla et al. ............... 424/725 |
| 7,897,384 B2 | 3/2011 | Binette et al. |
| 8,383,154 B2 | 2/2013 | Bar-Shalom et al. |
| 8,449,920 B2 | 5/2013 | Niichel |
| 8,518,448 B2 | 8/2013 | Niichel |
| 8,545,892 B2 | 10/2013 | Niichel |
| 2003/0138490 A1 | 7/2003 | Hu et al. |
| 2004/0158056 A1 | 8/2004 | Hiemstra et al. |
| 2004/0195710 A1* | 10/2004 | Hubbell ............... A61K 9/1635 264/4.1 |
| 2004/0224019 A1 | 11/2004 | Shefer et al. |
| 2006/0223776 A1 | 10/2006 | Frechet et al. |
| 2007/0149466 A1 | 6/2007 | Milburn et al. |
| 2007/0190209 A1 | 8/2007 | Sinnott |
| 2007/0196437 A1 | 8/2007 | Hamaker et al. |

FOREIGN PATENT DOCUMENTS

| | | |
|---|---|---|
| FR | 1522233 A | 4/1968 |
| GB | 1081667 A | 8/1967 |
| JP | 03 168359 | 1/1993 |
| JP | 06 055636 | 10/1995 |
| JP | 07 277032 | 4/1997 |
| WO | WO-9835992 A1 | 8/1998 |
| WO | WO-0032064 A1 | 6/2000 |
| WO | WO-02076244 A1 | 10/2002 |
| WO | WO-2005061611 A1 | 7/2005 |
| WO | WO-2006022585 A1 | 3/2006 |
| WO | WO-2007135114 A1 | 11/2007 |

OTHER PUBLICATIONS

Akiyoshi, K.; Sunamoto, J. Supramolecular assembly of hydrophobized polysaccharides. Supramolecular Science 1996, 3, 157-163.

Akiyoshi, K.; Taniguchi, I.; Fukui, H.; Sunamoto, J. Hydrogel nanoparticle formed by self-assembly of hydrophobized polysaccharide. Stabilization of adriamycin by complexation. European Journal of Pharmaceutics and Biopharmaceutics 1996, 42, 286-290.

Alhaique, F.; Coviello, T.; Rambone, G.; Carafa, M.; Murtas, E.; Riccieri, F. M.; Dentini, M.; Desideri, P. A gellan-scleroglucan co-crosslinked hydrogel for controlled drug delivery. Proceedings of the International Symposium on Controlled Release of Bioactive Materials 1998, 25th 866-867.

Augst, A; Kong H.J.; Mooney D.J. Alginate Hydrogels as Biomaterials. Macromol. Biosci. 2006, 6, 623-633.

Bajpai, S. K.; Sharma, S. Investigation of swelling/degradation behavior of alginate beads crosslinked with Ca2+ and Ba2+ ions. React. Func. Polym. 2004, 59, 129-140.

Barbucci, R.; Consumi, M.; Lamponi, S.; Leone, G. Polysaccharides based hydrogels for biological applications. Macromol. Symp. 2003, 204, 37-58.

Bassett, D.R. Jr., Howley, E.T. Limiting factors for maximum oxygen uptake and determinants of endurance performance. Med. Sci. Sports. Exerc. (2000) 32(1):70-84.

Belitz, H.-D. et al. Food Chemistry, 3rd ed., Springer-Verlag: Berlin, 2004, Chapter 4, p. 334.

Benedetti, L. M.; Topp, E. M.; Stella, V. J. Microspheres of hyaluronic acid esters-Fabrication methods and in vitro hydrocortisone release. J. Control. Rel. 1990, 13, 33-41.

Besheer, A.; Hause, G.; Kressler, J.; Mader, K. Hydrophobically modified hydroxyethyl starch: Synthesis, characterization, and aqueous self-assembly into nano-sized polymeric micelles and vesicles. Biomacromolecules 2007, 8, 359-367.

Cai, T.; Hu, Z.; Marquez, M. Synthesis and self-assembly of nearly monodisperse nanoparticles of a naturally occurring polymer. Langmuir 2004, 20, 7355-7359.

Cai, T.; Hu, Z.; Ponder, B.; St. John, J.; Moro, D. Synthesis and study of and controlled release from nanoparticles and their networks based on functionalized hydroxypropylcellulose. Macromolecules 2003, 36, 6559-6564.

Chakraborty, S.; Sahoo, B.; Teraoka, I.; Miller, L. M.; Gross, R. A. Enzyme-Catalyzed Regioselective Modification of Starch Nanoparticles. Macromolecules 2005, 38, 61-68.

Chakraborty, S.; Sahoo, B.; Teraoka, I.; Gross, R. A. Solution properties of starch nanoparticles in water and DMSO as studied by dynamic light scattering. Carbohydrate Polymers 2005, 60, 475-481.

Chemical, Biochemical and Engineering Thermodynamics Fourth Edition (2006), pp. 593-597, John Wiley & Sons, Inc., Stanley I. Sandler (editor).

Chen, J.; Jo, S.; Park, K. Polysaccharide hydrogels for protein drug delivery. Carbohydrate Polymers 1995, 28, 69-76.

Choy V.; Patel N.; Thibault J. Blood glucose monitor : An alternative off-line method to measure glucose concentration during fermentations with *Trichoderma reesei*. Biotechnology letters 2007, vol. 29, No. 7, pp. 1075-1080.

Coviello, et al. Polysaccharide Hydrogels for Modified Release Formulations. Journals of Controlled Release, Jan. 19, 2007, vol. 119, pp. 524; pg. 7.

Coviello, T.; Matricardi, P.; Marianecci, C.; Alhaique, F. Polysaccharide hydrogels for modified release formulations. J. Control. Rel. 2007, 119, 5-24.

Coviello, T.; Palleschi, A.; Grassi, M.; Matricardi, P.; Bocchinfuso, G.; Alhaique, F. Scleroglucan: A versatile polysaccharide for modified drug delivery. Molecules 2005, 10, 6-33.

Crawford. Effect of Carbohydrate and Carbohydrate-Protein Supplementation on Power Performance in Collegiate Football Players Performing a Simulated Game Task. Office of Graduate Studies of Texas A&M University, Dec. 2005; Abstract.

Crittenden, R.; Weerakkody, R.; Sanguansri, L.; Augustin, M. Synbiotic Microcapsules That Enhance Microbial Viability during Nonrefrigerated Storage and Gastrointestinal Transit. Applied and Environmental Microbiology, Mar. 2006, p. 2280-2282.

(56) References Cited

OTHER PUBLICATIONS

De Miguel I.; Rieumajou V.; Betbeder D. New methods to determine the extent of reaction of epichlorohydrin with maltodextrins. Carbohydrate Research 319 (1999) 17-23.

De Nooy, A. E. J.; Masci, G.; Crescenzi, V. Versatile synthesis of polysaccharide hydrogels using the Passerini and Ugi multicomponent condensations. Macromolecules 1999, 32, 1318-1320.

Dong, J; Chen L; Ding Y; Han W. Swelling and Mechanical Properties of a Temperature-Sensitive Dextran Hydrogel and its Bioseparation Applications. Macromol. Chem. Phys. 2005, 206, 1973-1980.

Dou, H.; Tang, M.; Yang, W.; Sun, K. One-pot synthesis, characterization, and drug loading of polysaccharide-based nanoparticles with carboxy functional groups. Colloid Polym. Sci. 2007, 285, 1043-1047.

Dumitriu, S.; Dumitriu, M. Hydrogels as support for drug delivery systems. In Polysaccharides in Medicinal Applications; Dumitriu, S. Ed.; Dekker: New York, 1996; pp. 705-764.

Edlund, U.; Albertsson, A.-C. A microspheric system: hemicellulose-based hydrogels. Journal of Bioactive and Biocompatible Polymers 2008, 23, 171-186.

Edman, P.; Björk, E. Routes of delivery: Case studies: (1) Nasal delivery of peptide drugs. Adv. Drug Delivery Rev. 1992, 8, 165-177.

Elfstrand L.; Eliasson, A.; Jonsson M.; Reslow M.; Wahlgren M.; From Starch to Starch Microspheres: Factors Controlling the Microspheres Quality, Starch 58 (2006) 381-390.

Gao, J.; Haidar, G.; Lu, X.; Hu, Z. Self-association of hydroxypropylcellulose in water. Macromolecules 2001, 34, 2242-2247.

Ghose, T.K. Measurement of Cellulase Activities, Pure & Appl. Chem., vol. 59, No. 2, pp. 257-268, 1987.

Gouyon F., Caillaud, L.; Carriere, V.; Klein, C.; Dalet, V.; Citadelle, D.; Kellett, G.L.; Thorens, B.; Leturque A.; Brot-Laroche E. Simple-sugar meals target GLUT2 at enterocyte apical membranes to improve sugar absorption: a study in GLUT2-null mice. J. Physiol (2003) 552.3, pp. 823-832.

Hadi, N. A.; Giouvanoudi, A.; Morton, R.; Horton, P. W.; Spyrou, N. M. Variations in gastric emptying times of three stomach regions for simple and complex meals using scintigraphy. IEEE Transactions on Nuclear Science 2002, 49, 2328-2331.

Han, J.; BeMiller, J.N. Preparation and physical characteristics of slowly digesting modified food starches. Carbohydrate Polymers 67 (2007) 366-374.

Harada, T. and Harada, A., Gel formation and ultrastructure in food polysaccharides. In Polysaccharide Association Structures in Foods, Walter, R.H., ed., Marcel Dekker: New York, 1998, Chapter 3, pp. 37-39.

Hashizaki, K; Taguchi H.; Itoh, C.; Sakai H.; Abe, M.; Saito Y.; Ogawa N. Effects of Poly(ethylene glycol).(PEG) Concentration on the Permeability of PEG-Grafted Liposomes. Chem. Pharm. Bull. 53(1) 27-31 (2005).

Hu, Z.; Lu, X.; Gao J.; Wang, C. Polymer Gel Nanoparticle Networks. Adv. Mater. 2000, 12, No. 16, 1173-1176.

Huang L.K.; Mehta R.C.; DeLuca, P.P. Evaluation of a Statistical Model for the Formation of Poly [Acryloyl Hydroxyethyl Starch] Microspheres, Pharmaceutical Research, vol. 14, No. 4, 1997.

Ichikawa, S.; Iwamoto, S.; Watanabe, J. Formation of biocompatible nanoparticles by self-assembly of enzymatic hydrolysates of chitosan and carboxymethyl cellulose. Biosci. Biotechnol. Biochem. 2005, 69, 1637-1642.

Ilium, L.; Farraj, N. F.; Fisher, A. N.; Gill, I.; Miglietta, M.; Benedetti, L. M. Hyaluronic acid ester microspheres as a nasal delivery system for insulin. J. Control. Rel. 1994, 29, 133-141.

Ilium, L.; Jorgensen, H.; Bisgaard, H.; Krogsgaard, O.; Rossing, N. Bioadhesive microspheres as a potential nasal drug delivery system. Int. J. Pharm. 1987, 39, 189-199.

Jain D.; Panda A.K.; Majumdar D.K. Eudragit S100 Entrapped Insulin Microspheres for Oral Delivery. AAPS PharmSciTech 2005; 6(1) Article 16, pp. E100-E107.

Jantas R. Synthesis and Characterization of Acryloyloxystarch, Journal of Applied Polymer Science, vol. 65, 2123-2129 (1997).

Kabra, B. G.; Gehrke, S. H.; Spontak, R. J. Microporous, responsive hydroxypropyl cellulose gels. 1. Synthesis and microstructure. Macromolecules 1998, 31, 2166-2173.

Kahovec, J et al. Pure Appl. Chem., 74(10): 1921-1956 (2002).

Kasaai, M.R. Calculation of viscometric constants, hydrodynamic volume, polymer-solvent interaction parameter, and expansion factor for three polysaccharides with different chain conformations. Carbohydrate Research 343 (2008) 2266-2277.

Kim, S. H.; Won, C. Y.; Chu, C. C. Synthesis and characterization of dextran-based hydrogel prepared by photocrosslinking. Carbohydrate Polymers 1999, 40, 183-190.

Klug E. D. Hydroxypropyl Cellulose. In Encyclopedia of Polymer Science and Technology; Bikales, N. M., Ed.; Wiley Interscience: New York, 1971; vol. 15, pp. 307-314.

Kong, H.; Mooney, D. J. Polysaccharide-based hydrogels in tissue engineering. In Polysaccharides, 2nd ed.; Dumitriu, S., Ed.; Dekker: New York, 2005; pp. 817-837.

Lee, K.; Heo, T. Survival of Bifidobacterium longum Immobilized in Calcium Alginate Beads in Simulated Gastric Juices and Bile Salt Solution. Applied and Environmental Microbiology, Feb. 2000, p. 869-873.

Leone, G; Barbucci R; Borzacchiello A; Ambrosio L; Netti P.A.; Migliaresi C. Preparation and physico-chemical characterization of microporous polysaccharidic hydrogels. Journal of Materials Science: Materials in Medicine 15 (2004) 463-467.

Madene, A.; Jacquot, M.; Scher, J.; Desobry, S. Flavour encapsulation and controlled release-a review. International Journal of Food Science and Technology 2006, 41, 1-21.

Magnani, A.; Rappuoli, R.; Lamponi, S.; Barbucci, R. Novel polysaccharide hydrogels: characterization and properties. Polym. Adv. Technol. 2000, 11, 488-495.

Maia, J.; Ferreira, L.; Carvalho, R.; Ramos, M.A.; Gil, M.H. Synthesis and characterization of new injectable and degradable dextran-based hydrogels. Polymer 46 (2005) 9604-9614.

Malafaya, P.B.; Stappers, F.; Reis, R.L. Starch-based microspheres produced by emulsion crosslinking with a potential media dependent responsive behavior to be used as drug delivery carriers. J. Mater Sci:Mater Med (2006) 17:371-377.

Marsano E.; Bianchi E.; Sciutto L. Microporous thermally sensitive hydrogels based on hydroxypropyl cellulose crosslinked with polyethyleneglicol diglycidyl ether. Polymer 44 (2003) 6835-6841.

Martindale, The Extra Pharmacopoeia, 28th ed.; The Pharmaceutical Press: London, 1982; pp. 1063-1072.

McEntee, M.-K. E.; Bhatia, S. K.; Tao, L.; Roberts, S. C.; Bhatia, S. R. Tunable transport of glucose through ionically-crosslinked alginate gels: effect of alginate and calcium concentration. J. Appl. Polym. Sci. 2008, 107, 2956-2962.

Meena, R.; Chhatbar, M.; Prasad, K.; Siddhanta, A. K. Development of a robust hydrogel system based on agar and sodium alginate blend. Polym. Int. 2008, 57, 329-336.

Meena, R.; Prasad, K.; Siddhanta, A. K. Preparation of genipin-fixed agarose hydrogel. J. Appl. Polym. Sci. 2007, 104, 290-296.

Mohamadnia, Z.; Zohuriaan-Mehr, M. J.; Kabiri, K.; Jamshidi, A.; Mobedi, H. pH-Sensitive IPN hydrogel beads of carrageenan-alginate for controlled drug delivery. J. Bioactive Compat. Polym. 2007, 22, 342-356.

Mohamadnia, Z.; Zohuriaan-Mehr, M. J.; Kabiri, K.; Jamshidi, A.; Mobedi, H. Ionically crosslinked carrageenan-alginate hydrogel beads. Journal of Biomaterials Science: Polymer Edition 2008, 19, 47-59.

Mooney, D. J. Polysaccharide-based hydrogels in tissue engineering. In Polysaccharides, 2nd ed.; Dumitriu, S., Ed.; Dekker: New York, 2005; pp. 817-837.

Nicholas, A.R.; Scott, M.J.; Kennedy, N.I.; Jones M.N. Effect of grafted polyethylene glycol (PEG) on the size, encapsulation efficiency and permeability of vesicles. Biochimica et Biophysica Acta 1463 (2000) 167-178.

(56) References Cited

OTHER PUBLICATIONS

Palleschi, A.; Coviello, T.; Bocchinfuso, G.; Alhaique, F. Investigation of a new scleroglucan/borax hydrogel: structure and drug release. Int. J. Pharm. 2006, 322, 13-21.
Park, H.; Park, K.; Shalaby, W. S. W. Chemical Gels. Biodegradable Hydrogels for Drug Delivery, 1st. ed.; Technomic Publishing Company: Lancaster, PA, 1993; Chapter 4, pp. 67-98.
Paul, W.; Sharma, C.P. Tricalcium Phosphate Delayed Release Formulation for Oral Delivery of Insulin: A Proof-of-Concept Study. Journal of Pharmaceutical Sciences, vol. 97, No. 2, Feb. 2008, pp. 875-882.
Petri B., Bootz A.; Khalansky A.; Hekmatara T.; Muller, R.; Uhl R.; Kreuter J.; Gelperina S. Chemotherapy of brain tumour using doxorubicin bound to surfactant-coated poly(butyl cyanoacrylate) nanoparticles: Revisiting the role of surfactants. Journal of Controlled Release 117 (2007) 51-58.
Picker-Freyer K.M.; Durig, T. Physical Mechanical and Tablet Formation Properties of Hydroxypropylcellulose: in Pure Form and in Mixtures. AAPS PharmSciTech 2007; 8 (4) Article 92, pp. E1-E-9.
Pitarresi, G.; Pierro, P.; Palumbo, F. S.; Tripodo, G.; Giammona, G. Photo-cross-linked hydrogels with polysaccharide-poly(amino acid) structure: New biomaterials for pharmaceutical applications. Biomacromolecules 2006, 7, 1302-1310.
Polymer Science and Technology Second Edition (2003), pp. 108-111, Prentice Hall Professional Technical Reference, Joel R. Fried (editor).
Polymer Physics, (2007), pp. 150-154, Oxford University Press, Michael Rubenstein and Ralph H. Colby (editors).
Reis, a. V.; Guilherme, M. R.; Moia, T. A.; Mattoso, L. H. C.; Muniz, E. C.; Tambourgi, E. B. Synthesis and characterization of starch-modified hydrogel as potential carrier for drug delivery system. J. Polym. Sci.: Part A: Polym. Chem. 2008, 46, 2567-2574.
Shibanuma, T et al. "Thermo sensitive Phase-Separation Behavior of Poly(acrylic acid)-graft-poly(N,N-dimethylacrylamide)AqueousSolution" Macromolecules (2000) 33:444-450.
Simi, C. K.; Abraham, T. E. Hydrophobic grafted and crosslinked starch nanoparticles for drug delivery. Bioprocess and Biosystems Engineering 2007, 30, 173-180.
Simkovic, I.; Hricovini M.; Sasinkova V. Preparation of ion-exchangers by cross-linking of starch or polygalacturonic acid with 1,3-bis(3-chloro-2-hydroxypropyl)imidazolium hydrogen sulphate. Carbohydrate Polymers 47 (2002) 131-136.
Sou, K.; Endo, T.; Takeoka, S.; Tsuchida E. Poly(ethylene glycol)-Modification of the Phospholipid Vesicles by Using the Spontaneous Incorporation of Poly(ethylene glycol)-Lipid into the Vesicles, Bioconjugate Chem. 2000, 11, 372-379.
Stmark E.; Harrisson S.; Wooley K.L.; Malmstrom E.E. Comb Polymers Prepared by ATRP from Hydroxypropyl Cellulose. Biomacromolecules 2007, 8, 1138-1148.
Taluja A.; Youn, Y.S.; Bae, Y. H.; Novel approaches in microparticulate PLGA delivery systems encapsulating proteins; J. Mater, Chem., 2007, 17, 4002-4014.
Thielemans, W.; Belgacem, M. N.; Dufresne, A. Starch nanocrystals with large chain surface modifications. Langmuir 2006, 22, 4804-4810.
Triton Nutrition, Information on Taking Creatine Supplements. Created Sep. 30, 2005. [Online], [retrieved on Jan. 25, 2009]. Retrieved from the internet URL:http://searchwarp.com/swa19262.htm>; p. 1, para 3.
Tsapis, N.; Bennett, D.; Jackson, B.; Weitz, D.A.; Edwards, D.A. Trojan particles: Large porous carriers of nanoparticles for drug delivery. PNAS, Sep. 17, 2002, vol. 99, No. 19, 12001-12005.
Van Krevelen, D W and TE Nijenhuis K, Properties of Polymer Fourth Edition (2009) pp. 210-212.
Van Thienen, T.G.; Demeester, J.; De Smedt; S.C.; Screening poly(ethyleneglycol) micro- and nanogels for drug delivery purposes, International Journal of Pharmaceutics 351 (2008) 174-185.
Vieira, E. F. S.; Cestari, A. R.; Airoldi, C.; Loh, W. Polysaccharide-based hydrogels: Preparation, characterization and drug interaction behavior. Biomacromolecules 2008, 9, 1195-1199.
Walter, R.H. Polysaccharide Dispersions: Chemistry and Technology in Food, Academic Press: San Diego, 1998, Chapter 8, pp. 177-178.
Weng, H.; Zhou, J.; Tang, L.; Hu, Z. Tissue responses to thermally-responsive hydrogel nanoparticles, J. Biomater. Sci. Polymer Edn, vol. 15, No. 9, pp. 1167-1180 (2004).
Woo, B. H.; Jiang, G.; Jo, Y. W.; DeLuca, P. P. Preparation and characterization of a composite PLGA and poly(acryloyl hydroxyethyl starch) microsphere system for protein delivery. Pharmaceutical Research 2001, 18, 1600-1606.
Xie, S. X.; Liu, Q.; Cui, S. W. Starch modification and application. In Food Carbohydrates: Chemistry, Physical Properties, and Applications; Cui, S. W. Ed.; Taylor & Francis: New York 2005; p. 358-404.
Yoo, H.S.; Lee, E.A.; Yoon, J.J.; Park, T.G. Hyaluronic acid modified biodegradable scaffolds for cartilage tissue engineering. Biomaterials 26 (2005) 1925-1933.
Yu, X. J.; Hoffman, A. S. Polysaccharide hydrogels as drug delivery matrixes. Proceedings of the 22nd International Symposium on Controlled Release of Bioactive Materials, 1995; Controlled Release Society; pp. 352-353. -.
Zhang, L.; Yang, C.; Yan, L. Perspectives on: Strategies to Fabricate Starch-based Hydrogels with Potential Biomedical Applications. Journal of Bioactive and Compatible Polymers, vol. 20, May 2005, p. 297-314.

* cited by examiner

Carboxymethyl cellulose

Alginic acid

Hyaluronic acid

SUSTAINED RELEASE OF NUTRIENTS IN VIVO

CROSS-REFERENCE TO RELATED APPLICATIONS

This application is a continuation application of U.S. application Ser. No. 12/337,022, filed Dec. 17, 2008, now U.S. Pat. No. 8,563,066, which claims the benefit of priority of U.S. provisional patent application Ser. No. 61/014,251 filed Dec. 17, 2007.

The foregoing application, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The invention relates to compositions for increasing performance of athletes by providing appropriately timed release and increased absorption of nutrients including carbohydrates, amino acids, and electrolytes.

BACKGROUND OF THE INVENTION

Contemporary understanding of sports related nutritional requirements indicates that carbohydrate consumption plays a key role improving athlete endurance and performance. With the entrance of Gatorade® and other similar sports drinks beginning in the mid 1960's more attention has been paid to understanding the role of various nutrients on human performance in athletic events.

Understanding the body's ability to absorb and process carbohydrates and other nutrients for maximal performance output has been studied by many. In 2003, the International Olympic Committee on Nutrition for Athletes issued a position stating that a high carbohydrate diet in the days before competition helps enhance performance, particularly when exercise lasts longer than about 60 min and that athletes should aim to achieve carbohydrate intakes that meet the fuel requirements of their training programs and also adequately replace their carbohydrate stores during recovery between training sessions and competition. However, this is a difficult task, especially for athletes in training who need a sustained supply of carbohydrates and other nutrients without the drawback of an intake of large amounts or smaller amounts but at more regular intervals, of food in order to meet the dietary requirements necessary to maintain enhanced performance.

There is thus a need in the art to provide a sustained and controlled supply of carbohydrates and other nutrients to individuals without the necessity of intake of excess food and snacks.

Citation or identification of any document in this application is not an admission that such document is available as prior art to the present invention.

SUMMARY OF THE INVENTION

The present invention is based upon the premise that athletic performance can be improved by providing controlled release of nutritional supplements (such as carbohydrates and electrolytes).

The present invention relates to a composition comprising nutritional supplements (such as carbohydrates, amino acids, vitamins, and/or electrolytes), which when administered to a human provides a sustained release of the nutritional supplements over an extended period of time. Preferably, the nutritional supplements may be delivered in a sustained and extended manner for peak athletic performance and recovery. For instance, the composition may release the nutritional supplements so that absorption and oxidation rates of exogenous carbohydrates are increased during exercise. According to one embodiment, the composition releases nutritional supplements such that saturation of the SGLT1 and GLUT-5 transporters with exogenous carbohydrates is maintained during exercise.

In a preferred embodiment, a composition for in vivo consumption may comprise nutritional supplements; and, compounds for sustained release of the nutritional supplements in vivo. Preferably, the nutritional supplements may comprise carbohydrates, amino acids, vitamins, and electrolytes.

In another preferred embodiment, the compounds for the sustained release of the nutritional supplements may comprise one or more components selected from biodegradable polymers, bioadhesives, nanoparticles, colloidal suspensions and binders.

According to one embodiment, the biodegradable polymers and binders may be selected from poly(lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and polyorthoester, biodegradable polyurethanes, hydrogels, blends and copolymers thereof.

In an advantageous embodiment, the invention encompasses nanoparticles and microparticles comprising hydrogels. Advantageously, the hydrogels may comprise modified polysaccharides. The polysaccharides may comprise modifications with chemical groups such as carboxylic acid (as in carboxymethyl cellulose [CAS no. 9000-11-7], starch glycolate [CAS no. 9057-06-1], etc.), acryloyl or methacryloyl (as in starch acrylate [CAS no. 39316-65-9], hydroxypropyl cellulose acrylate [CAS no. 94187-94-7], hydroxyethyl starch acrylate, etc.), hydroxyalkyl (as in hydroxypropyl cellulose [CAS no. 9004-64-2], hydroxyethyl starch [CAS no. 9005-27-0], hydroxyethyl cellulose [CAS no. 9004-62-0], etc.), and ester (as in starch acetate, starch phosphate, etc.). The modified starch may also contain grafted fatty acid moieties (as in starch adipate [CAS no. 39347-22-3], etc.), oligo(alkylene oxide) grafts (as in hydroxypropyl cellulose, etc.), grafted hydrophobes such as cholesterol, grafted amphiphiles such as alkenylsuccinate (as in 1-octenylsuccinic acid anhydride modified starch, etc.) or side chain derivatizations to introduce aldehydic or carboxylic groups.

In another advantageous embodiment, the invention may also comprise methods of crosslinking of the microparticles and nanoparticles of the present invention to form hydrogels. Crosslinking may be performed using free radical initiators such as persulfate salts, or redox systems involving ascorbic acid, or a naturally occurring crosslinker such as genipin. Ionic crosslinking may also be contemplated, such as with anionic polysaccharides such as gellan.

In another yet advantageous embodiment, the invention may also comprise the preparation of hydrogels. In an advantageous embodiment, a blend of hydrophobically modified polysaccharide such as, but not limited to, hydroxypropyl cellulose and a carboxy containing polysaccharide such as, but not limited to, alginate or carboxymethyl cellulose may be used to prepare the hydrogel particles of the present invention. In another advantageous embodiment, nanoparticle suspensions may be synthesized by self-assembly of chitosan and carboxymethyl cellulose hydrolysate, wherein the polymers may be hydrolyzed with the enzymes chitosanase and cellulase, respectively.

In another embodiment, hydrogels may be prepared from mixtures of acidic polysaccharides such as, but not limited to, alginates, and basic polysaccharides such as, but not limited to, oligosaccharide derivatives of chitosan; a basic polysaccharide such as, but not limited to, chitosan and anionic polysaccharide such as, but not limited to, hyaluronic acid; alginate and oxidized alginate blended with chitosan; grafted agar and sodium alginate blend with acrylamide; gellan co-crosslinked with scleroglucan; photo-crosslinked modified dextran; starch reacted with glycidyl methacrylate; or polymerizable saccharide monomers, such as sucrose, created by reaction of the sugar with epoxy acrylate, or methacryloyl chloride and acetyl chloride. The nanoparticle and microparticle hydrogels may be prepared using polymer self-assembly (temperature, pH, or ionic strength induced precipitation; micelle formation; colloidal precipitation because of electrostatic interactions between oppositely charged polymers) or conventional emulsification-based methods.

In another preferred embodiment, the nutritional supplements are released in vivo in a sustained manner and in a concentration effective to increase exercise duration and cumulative power output potential by at least about 1% to about 50%, about 50% to about 100%, about 100% to about 500% or about 500% to about 1000% when compared to a control with no nutritional supplement ingestion pre and during exercise.

In another preferred embodiment, the nutritional supplements are released in vivo in a sustained manner and in a concentration effective to increase burst energy duration and power output by about 1% to about 50%, about 50% to about 100%, about 100% to about 500% or about 500% to about 1000% when compared to a control with no nutritional supplement ingestion before and during exercise.

In another preferred embodiment, the nutritional supplements are released in vivo in a sustained manner and in a concentration effective to increase burst energy duration and power output by about 1% to about 50%, about 50% to about 100%, about 100% to about 500% or about 500% to about 1000% when compared to a control with no nutritional supplement ingestion pre and during exercise.

In yet another preferred embodiment, the nutritional supplements are released in vivo in a sustained manner and in a concentration effective to increase the number of effective burst events by at least about 1% to about 50%, about 50% to about 100%, about 100% to about 500% or about 500% to about 1000% when compared to a control with no nutritional supplement ingestion pre and during exercise.

In another preferred embodiment, the nutritional supplements are released in vivo in a sustained manner and in a concentration effective to decrease the duration of recovery time between burst events by at least about 1% to about 50%, about 50% to about 100%, about 100% to about 500% or about 500% to about 1000% when compared to a control with no nutritional supplement ingestion before and during exercise.

In another preferred embodiment, the nutritional supplements are released in vivo in a sustained manner and in a concentration effective to increase continuous exercise power output (watts) by about 1% to about 50%, about 50% to about 100%, about 100% to about 500% or about 500% to about 1000%, advantageously about 50% at about $VO_2$ 62% for 90 minutes and not less than about 25% increase in high intensity (burst) exercise, about $VO_2$ 86%, power output and duration following 90 min of continuous exercise, and increase the number of effective "burst" periods by about 100% as compared to performance when utilizing commercially available performance enhancing drinks.

In yet another preferred embodiment, the compounds for sustained release of the nutritional supplements in vivo release the nutritional supplements in effective amounts and concentrations over extended periods of time to increase exercise duration and cumulative power output potential by about 1% to about 50%, about 50% to about 100%, about 100% to about 500% or about 500% to about 1000%, advantageously at least about 10% to about 70%, increase burst energy duration and power output by at least about 10% to about 70%, increase the number of effective burst events from about 10% to 100%, decreases the duration of recovery time between burst events by at least about 10% to about 100%, when compared to a control with no nutritional supplement ingestion pre and during exercise.

In another preferred embodiment; the compounds for sustained release of the nutritional supplements in vivo release the nutritional supplements in effective amounts and concentrations over extended periods of time to decrease duration of recovery time between burst events by at least about 2%, about 5%, about 10%, about 20%, about 30%, about 40%, about 50%, about 60%, about 70%, about 80%, about 90% or about 100% when compared to a control with no nutritional supplement ingestion pre and during exercise.

In another preferred embodiment, the compounds for sustained release of the nutritional supplements in vivo release the nutritional supplements in effective amounts and concentrations over extended periods of time to increase continuous exercise power output (watts) by about 2%, about 5%, about 10%, about 20%, about 30%, about 40%, about 50%, about 60%, about 70%, about 80%, about 90% or about 100%, advantageously about 50% at about $VO_2$ 62% for 90 minutes and not less than about a 25% increase in high intensity (Burst) exercise, about $VO_2$ 86%, power output and duration following 90 minutes of continuous exercise, and increase the number of effective burst periods by at least about 100% as compared to performance when utilizing commercially available performance enhancing drinks.

In another preferred embodiment, the compositions are formulated as a beverage, a gum, a food snack, a powder or any other consumable.

In another preferred embodiment, a method of improving athletic performance and endurance comprises administering to an individual a composition comprising nutritional supplements and, compounds for sustained release of the nutritional supplements in vivo, wherein the nutritional supplements comprise carbohydrates, amino acids, vitamins, and electrolytes; and, consuming the composition wherein the compounds for sustained release of the nutritional supplements in vivo release the nutritional supplements in effective amounts and concentrations over extended periods of time to increase exercise duration and cumulative power output potential by at least about 1% to about 50%, about 50% to about 100%, about 100% to about 500% or about 500% to about 1000% about 10% to about 70%, increase burst energy duration and power output by at least about 10% to about 70%, increase the number of effective burst events from about 10% to 100%, decreases the duration of recovery time between burst events by at least about 10 to about 100%, when compared to a control with no nutritional supplement ingestion before and during exercise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which.

DETAILED DESCRIPTION

Figure 1:
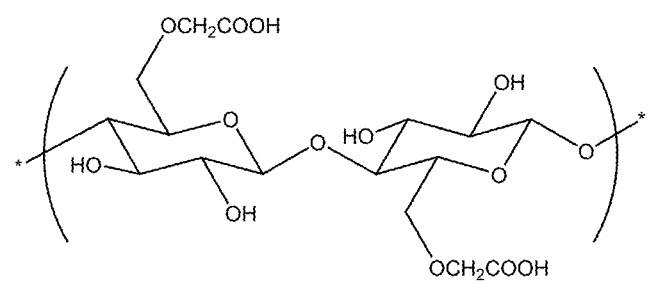
FIG. 1 depicts polysaccharides containing carboxylic acid groups.
Figure 1:
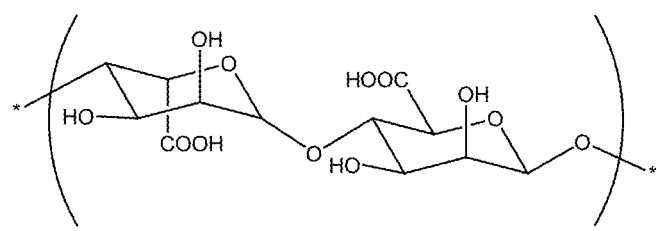
Figure 1:
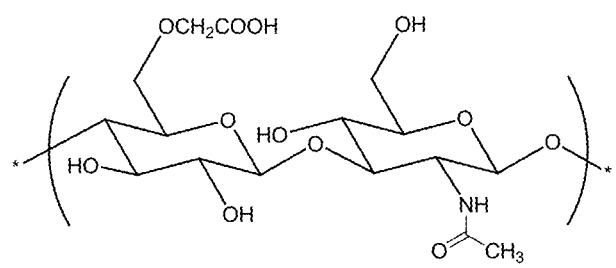

While the making and using of the various embodiments of the present invention are discussed in detail below, it should be appreciated that the present invention provides many applicable inventive concepts which can be embodied in a wide variety of specific contexts. The specific embodiments described herein are merely illustrative of specific ways to make and use the invention and do not delimit the scope of the invention or the scope of the claims appended hereto.

According to one embodiment, the composition of the present invention provides sustained release over extended periods of time of carbohydrates and optionally other nutrients to an individual. Preferably, carbohydrates are released from the composition in a manner which maintains maximum carbohydrate absorption and oxidation rates for a prolonged period of time. Generally, the maximal carbohydrate absorption rate in an individual is in a range of about 1.2 to about 1.7 g/min. A peak carbohydrate oxidation rate of about 1.75 g/min can be achieved, for example, when carbohydrates are administered as a blend of glucose (1.2 g/min) and fructose (0.8 g/min). See, e.g., Azevedo, J. L. Jr.; Tietz, E.; Two-Feathers, T.; Paull, J.; Chapman, K. Lactate, Fructose and Glucose Oxidation Profiles in Sports Drinks and the Effect on Exercise Performance. PLoS ONE [Online] 2007, 2, pp e927-e927 (doi:10.1371/journal-.pone.0000927), for representative carbohydrate oxidation profiles.

The rate and extent of exogenous carbohydrate absorption may be limited not only by the amount of carbohydrate available but also by the maximum intestinal transport capacity for glucose and fructose. Intestinal transport of glucose is mediated by a sodium dependent glucose transporter (SGLT1), located in the brush-border membrane. SGLT1 transporters may become saturated at a glucose ingestion rate of ~1 g/min. Fructose on the other hand is absorbed from the intestine by GLUT-5, a sodium-independent facilitative fructose transporter. Generally, ingestion of a mixture of carbohydrates that have different transport mechanisms for absorption in to the blood stream, simultaneously increases carbohydrate and water absorption.

Applicants have approximated the number of calories required based on certain activity levels as indicated in Table 1. The energy requirement is estimated based on the weight-normalized Caloric burn rate (kcal per minute of activity per unit body mass of an individual) and the Caloric content of glucose (~4 kcal/g). The energy available from exogenous glucose oxidation is about 396 kcal. As can be seen from Table 1, this energy is insufficient to meet the total energy requirement of the listed activities. The present invention seeks to narrow the Caloric gap using a controlled-release nutrient formulation.

TABLE 1

Energy requirement based on activity levels

|  | Competitive soccer | Running (8.5 min/mile) | Running (12 min/mile) | Outside construction work |
|---|---|---|---|---|
| Caloric burn rate (kcal $min^{-1}$ $lb^{-1}$) | 0.0757 | 0.0871 | 0.0606 | 0.0417 |
| Total energy required* (kcal) | 1022 | 1176 | 818 | 563 |
| Required glucose oxidation rate$^§$ (g $min^{-1}$ $lb^{-1}$) | 0.0189 | 0.0218 | 0.0151 | 0.0104 |
| Total glucose required* (g) | 256 | 294 | 204 | 141 |
| Exogenous glucose oxidized[#] (g) | 99 | 99 | 99 | 99 |
| Difference (g) | 157 | 195 | 105 | 42 |

TABLE 1-continued

Energy requirement based on activity levels

|  | Competitive soccer | Running (8.5 min/mile) | Running (12 min/mile) | Outside construction work |
|---|---|---|---|---|
| Energy obtained from exogenous glucose (kcal) | 396 | 396 | 396 | 396 |
| Caloric gap (kcal) | 627 | 780 | 422 | 167 |

*Based on a 150-lb individual and a 90-min activity.
§Oxidation rate of glucose that is required to sustain the Caloric burn rate reported in row 1. The values are estimated using the fact that 1 g of pure carbohydrate yields about 4 kcal of energy.
Based on an exogenous glucose oxidation rate of ~1.1 g/min, which is determined by the rate of transport of glucose (from the intestinal lumen in to the blood stream) across the intestinal epithelium.

The term "sustained release" (i.e., extended release and/or controlled release) are used herein to refer to nutritional supplement, for example carbohydrates etc., delivery system or composition that is introduced into the body of a human and that continuously releases a stream of one or more nutrients over a predetermined time period and at a level sufficient to achieve a desired effect throughout the predetermined time period. Reference to a continuous release stream is intended to encompass release that occurs as the result of diffusion-limited release of the component from the matrix, or biodegradation in vivo of the composition, or a matrix or component thereof, or as the result of metabolic transformation or dissolution of the added nutrients or other desired agent(s). Delayed release may be achieved by entrapping the nutrients within particulate carriers with mucoadhesive surface characteristics. Adhesion of the nutrient-loaded particles to intestinal mucosa will increase retention time of the particles inside the intestinal lumen, thereby providing continuous release and transport of nutrients across the epithelium into blood, beyond the normal retention time of non-adhesive composition inside the gastrointestinal tract.

In a preferred embodiment, the nutritional supplement composition is in the form of a solution, suspension, gel capsule, powder, snack (e.g. a bar), granola form, or tablet. The "delivery" of nutrients comprises, for example, suspending the nutrients individually or in combinations in sustained release particulate microparticles; compounds which bind to the nutrients with different affinities and the like. According to one embodiment, the requisite volume for consumption by the individual is about 500 mL when in liquid form, however, formulations increasing and or decreasing the concentrations and amounts are contemplated.

Examples of nutrients include, but not limited to carbohydrates, proteins, amino acids, vitamins, co-enzymes, phospholipids, minerals, and electrolytes. Examples of vitamins and co-enzymes that may be delivered using this invention include but are not limited to water or fat soluble vitamins such as thiamin, riboflavin, nicotinic acid, pyridoxine, pantothenic acid, biotin, flavin, choline, inositol and paraminobenzoic acid, carnitine, vitamin C, vitamin D and its analogs (such as ergocalciferol, calcitriol, doxercalciferol, and paricalcitol), vitamin A and the carotenoids, retinoic acid, vitamin E and vitamin K.

In a preferred embodiment, the nutritional composition comprises carbohydrates that are taken up by different receptors, e.g. SGLT and GLUT receptors. Suitable carbohydrates include, but are not limited to, mono-, di- and polysaccharides such as glucose, sucrose, maltose as well as more complex edible carbohydrates such as maltodextrins. According to one preferred embodiment, the composition includes a blend of glucose and fructose. The weight ratio of glucose to fructose preferably ranges from about 1:1 to about 100:1, about 5:1 to about 95:1, about 10:1 to about 90:1, about 15:1 to about 85:1, about 20:1 to about 80:1, about 25:1 to about 75:1, about 30:1 to about 70:1, about 35:1 to about 65:1, about 40:1 to about 60:1, about 45:1 to about 55:1 or about 50:1. Preferably, the composition includes from about 0.1 to about 99.9 wt. %, about 1 to about 99 wt. %, about 5 to about 95 wt. %, about 10 to about 90 wt. %, about 15 to about 85 wt. %, about 20 to about 80 wt. %, about 25 to about 75 wt. %, about 30 to about 70 wt. %, of carbohydrates, about 35 to about 65 wt. %, about 40 to about 60 wt. %, about 45 to about 55 wt. %, or about 50 wt. %, calculated on a 100% dry matter basis of the composition.

In another preferred embodiment, the composition includes amino acids. The amino acids may be in the form of free amino acids or peptides, and are preferably present in an amount in the range of from about 0.1 to about 99.9 wt. %, about 1 to about 99 wt. %, about 5 to about 95 wt. %, about 10 to about 90 wt. %, about 15 to about 85 wt. %, about 20 to about 80 wt. %, about 25 to about 75 wt. %, about 30 to about 70 wt. %, of carbohydrates, about 35 to about 65 wt. %, about 40 to about 60 wt. %, about 45 to about 55 wt. %, or about 50 wt. % calculated on a 100% dry matter basis of the composition.

The peptide material can be derived from proteins of animal or plant origin and examples of such proteins are milk proteins, meat proteins, soy proteins, wheat proteins, pea proteins, rice proteins and maize proteins. Preferably the protein raw material is wheat gluten protein or a subfraction thereof such as gliadin. In the present context, the term "peptide material" is understood to indicate a protein hydrolysate and may contain all types of peptides that may vary in length as well as a certain amount of free amino acids resulting from the hydrolysis. The protein raw material is hydrolyzed by one or more hydrolytic enzymes. The hydrolytic enzyme can be of animal, plant, yeast, bacterial or fungal origin. Preferably enzyme preparations are used which have a low exo-peptidase activity to minimize the liberation of free amino acids and to improve taste profiles of the protein hydrolysates. The preferred hydrolyzed protein material of the present invention has an average peptide chain length in the range of 1-40 amino acid residues and more preferably in the range of 1-20 amino acid residues. The average peptide chain can be determined using the method as described in WO 96/26266. Further the peptide material is present in an amount of about 0.1-90 wt. %, calculated on dry matter basis of the composition.

Other optional components of the composition according to the invention are vitamins, minerals, electrolytes, flavors, antioxidants, components having co-enzyme and antioxidant properties, lipids including emulsifiers, and proteins for meeting specific nutritional and/or physiological needs.

In another preferred embodiment, the nutritional composition comprises a binder and/or biodegradable polymer or mixture of biodegradable polymers with appropriate time release characteristics and release kinetics. The composition of the invention may then be formed into a microparticles comprising the appropriate nutritional compositions suitable for providing efficacious concentrations of the compounds of the invention over a prolonged period of time without the need for frequent re-dosing. The composition of the present invention can be incorporated into the biodegradable polymer or polymer mixture in any suitable manner known to one of ordinary skill in the art and may form a homogeneous matrix with the biodegradable polymer.

In another preferred embodiment, the nutrient supplements are present in nano suspensions/colloidal particles. The nanoparticles or colloidal particles (CP) can form a stable colloidal suspension in water and in a physiological medium. The CP associate with the nutrients, e.g. carbohydrates, in aqueous media by a spontaneous mechanism; and the CP release the nutrients in a physiological medium and, more precisely, in vivo. The release kinetics depend on the nature of the polymer that is the CP precursor. A protein, whose nutritional value depends on the tertiary structure of the molecule may also be delivered by this method, using biocompatible polymer hosts that will not denature the protein.

Thus, by varying the specific structure of the polymers, it is possible to control the association and release phenomena from the kinetic and quantitative points of view.

Another preferred embodiment of the invention concerns the preparation of: selected particles; and other selected particles which are structured, submicron and capable of being used especially for carrying one or more nutrients, these particles being individualized (discrete) supramolecular arrangements that are: based on linear amphiphilic polyamino acids having peptide linkages and comprising at least two different types of hydrophilic repeating amino acids, and hydrophobic repeating amino acids, the amino acids of each type being identical to or different from one another; capable of associating at least one nutrient in colloidal suspension, in the undissolved state, and releasing it, especially in vivo in a prolonged and/or delayed manner; and stable in the aqueous phase at a pH of between 4 and 13, in the absence of surfactant(s).

Preferably, the particles are submicron structured particles capable of being used especially for carrying one or more nutrients, these particles being discrete supramolecular arrangements; capable of associating at least one nutrient in colloidal suspension, in the undissolved state, and releasing it, especially in vivo, in a prolonged and/or delayed manner; and stable in the aqueous phase at a pH of between 4 and 13, in the absence of surfactant(s).

In another preferred embodiment, the composition can be formulated to encapsulate the nutritional compositions in microspheres or microparticles so that it may be admixed or formulated into any form, such as a powder, a beverage, gum, nutritional food product, pill and the like.

A "microsphere" or "microparticle", as defined herein, includes a particle of a biocompatible solid-phase material having a diameter of about one millimeter to about one micrometer, or less, wherein the particle may contain a biologically active agent and, wherein the solid-phase material sustains the in vivo release of the nutritional compositions from the microsphere. A microsphere can have a spherical, non-spherical or irregular shape. The typical microsphere shape is generally spherical.

A "biocompatible" material, as defined herein; means that the material, and any degradation products of the material, is non-toxic to the recipient and also presents no significant deleterious or untoward effects on the recipient's body.

In a preferred embodiment, the microspheres contain a mixture of nutritional compounds and the microsphere is composed of a biodegradable material that is released over a certain period of time. For example, in order to provide an initial burst of nutrients to provide an immediate reservoir of energy or nutrients to the individual, the nutritional compounds are formulated as such and can contain a variety of carbohydrates, amino acids, electrolytes, vitamins, etc. in differing ratios. The second group can contain a differing ratio of carbohydrates:amino acids:vitamins etc., or strictly different or similar carbohydrates that are released over a longer period of time to maintain a sustainable release of the nutrients. The formulation of the nutrients in the microspheres and the timing of release can be varied depending on the types of activity, the individual, age, weight and nutritional needs. For example, a marathon runner (sustained nutrition over long period) would have different nutritional needs to a sprinter (burst of nutrition).

In another preferred embodiment, different types of carbohydrates, e.g. those that are taken up by for example, SGLT transporters versus GLUT transporters are added in differing ratios at differing release rates to achieve the results as described infra.

In another preferred embodiment, compositions comprise compounds which dissolve over a period of time in vivo sequentially in acid, neutral and weak alkaline regions of the gastrointestinal tract. These compounds include for example, an acidic polymeric dispersion coating as the first coating to prolong nutrient supplement release. In this embodiment, the microparticle comprises as a core a material comprising calcium carbonate, sugar, dextrose and nonpareil seeds. The first coating is a material which retards rapid passage of water. The first coating is preferably an aqueous dispersion of poly(methacrylic acid-co-ethyl acrylate) (commercially available under the designation Eudragit L30D-55). The second coat is a latex acrylic polymer. The second coating is preferably poly(ethyl acrylate-co-methyl methacrylate-co-2-trimethylammonioethyl methacrylate chloride) (commercially available under the designation Eudragit RS-30D). The thickness of the second coating is established to achieve the desired time-release rate for the drug.

The time release products are preferably substantially spherical in configuration. The diameter of the time release drug products typically ranges between 20 and 650 microns, between 30 and 500 microns or between 40 and 350 microns and is preferably between about 50 and 250 microns when the products are in a liquid suspension form. It is a feature of the present invention that the time release nutrient composition containing products of the present invention, because of their size, can be suspended in an aqueous medium, thereby providing a liquid suspension.

In this embodiment, the nutrient compositions are formulated as a time release formulation comprising: a core which can be optional; nutritional supplements bound to the core; a first coating having limited permeability to water; and a second coating, which is more permeable to water than the first coating, wherein the first and second coatings together comprise the time release components of the nutrient compositions.

The core will generally have a diameter of about 19 to 57, about 20 to 56, about 21 to 55, about 22 to 54, about 23 to 53, about 24 to 52, about 25 to 51, about 26 to 50, about 27 to 49, about 28 to 48, about 29 to 47, about 30 to 46, or about 31 to 45 microns. The core is generally comprised of an inert ingredient, preferably a material selected from the group consisting of calcium carbonate, sugar, dextrose and nonpareil seeds.

The first coating, which has a limited permeability to water and which retards rapid passage of acid and water. This first coating will typically have a diameter of between about 1.30 and 4.60, about 1.40 and 4.50, about 1.50 and 4.40, about 1.60 and 4.30, about 1.70 and 4.20, about 1.80 and 4.10, about 1.90 and 4.00, about 2.00 and 3.90, about 2.10 and 3.80, about 2.20 and 3.70, about 2.30 and 3.60 or about 2.40 and 3.50 microns. The first coating is preferably an acidic polymeric dispersion coating which prolongs drug release, more preferably an aqueous dispersion of poly (methacrylic acid-co-ethyl acrylate). Such a polymer is commercially available under the name EUDRAGIT L30D-55. The core and first coating together typically have a diameter of between about 60 and 77, about 61 and 76, about 62 and 75, about 63 and 74, about 64 and 75 or about 65 and 74 microns.

It is appreciated that the first and second coatings together comprise the time release components of the product of the present invention. The first and second coatings together effect time release of the orally administrable drug within an individual over a maximum period of about 12 hours. It is appreciated by those skilled in the art that the thickness of the second coating can be altered to achieve the desired time release rate for the supplement. That is, the thickness of the second coating can be increased to achieve a longer period of time release in the body. The coatings work due to differential porosity. The inner coating comprised of, for example, poly(methacrylic acid-co-ethyl acrylate) is sensitive to pH. Nutrient transport across the inner coating is determined by the porosity and water content of the coating, both of which are determined by the different pH values within regions of the gastrointestinal tract. In an acidic environment (in the stomach), the inner coating becomes relatively hydrophobic and shrinks, leading to decreased pore size and nutrient permeability. In contrast, the pH inside the intestinal lumen is higher. The inner coating becomes relatively hydrophilic due to ionization, and allows faster release of nutrients from the particle cores. The outer coating is not pH-responsive, but can be used to control nutrient permeability by controlling the pore size. The present invention provides in the first and second coating porosity such that water entering the time release component will pass through the second coating more rapidly that through the first coating and the drug and water exiting the time-release component will pass through the first coating more slowly than through the second coating. In the preferred form, passage through each coating is by mechanical means with the passage through the first coating being augmented by ionic interaction.

In another preferred embodiment, one or more of nutrient supplements are bound or encapsulated by a particle which is stable in an aqueous environment and are released over an extended period of time once the supplements have been consumed.

The composition according to the invention may have the form of a powder, gum, a beverage or any other food product. A beverage according to the invention can be prepared by dissolving the above-defined ingredients in an appropriate amount of water. Preferably an isotonic drink has been prepared. For drinks; intended to be used during and after exercise it is recommended to have a concentration of the composition according to the invention in the range of about 0.10-60 wt. % calculated on the total weight of the drink.

In a preferred embodiment, the formulation has a viscosity and "mouth-feel" approximately equivalent to water. The viscosity of the formulation can be quantified using a capillary viscometer, such as the Ubblehold viscometer, by determining the time required for the liquid to fall from one fiducial mark to another in a glass capillary [See, e.g., Pearce, E. M.; Wright, C. E.; Bordoloi, B. K. *Laboratory Experiments in Polymer Synthesis and Characterization*; Pennsylvania State University: University Park, 1982; p. 187]. Room temperature viscosity of water is about 1 cP, while that of olive oil is about 80 cP, castor oil about 1000 cP and corn syrup about 1400 cP. The viscosity of fat-free milk is about 30 cP [Vesa, T. H.; Marteau, P. R.; Briet, F. B. et al. *Am. J. Clin. Nutr.* 1997, 66, 123-126].

In another preferred embodiment; the composition comprises flavoring agents which provide a variety of tastes/aromas that are pleasant, palatable and impart a feeling of confidence for adults, adolescents, and child consumers.

In one preferred embodiment, consumption of the nutrient compositions increases exercise duration and cumulative power output potential by at least about 2%, about 5%, about 10%, about 20%, about 30%, about 40%, about 50%, about 60%, about 70%, about 80%, about 90% or about 100% when compared to no supplemental carbohydrate (i.e. the nutrient compositions) ingestion pre and during exercise.

In another preferred embodiment, consumption of the nutrient compositions increases burst energy duration and power output by at least about 2%, about 5%, about 10%, about 20%, about 30%, about 40%, about 50%, about 60%, about 70%, about 80%, about 90% or about 100% when compared to no supplemental carbohydrate ingestion pre and during exercise.

In another preferred embodiment, consumption of the nutrient compositions increases the number of effective burst events by at least about 1% to about 50%, about 50% to about 100%, about 100% to about 500% or about 500% to about 1000% when compared to no supplemental carbohydrate (i.e. the nutrient compositions) ingestion pre and during exercise.

In another preferred embodiment, consumption of the nutrient compositions decreases the duration of recovery time between burst events by at least about 2%, about 5%, about 10%, about 20%, about 30%, about 40%, about 50%, about 60%, about 70%, about 80%, about 90% or about 100% when compared to no supplemental carbohydrate (i.e. the nutrient compositions) ingestion pre and during exercise.

In another preferred embodiment, consumption of the nutrient compositions results in about 1% to about 50%, about 50% to about 100%, about 100% to about 500% or about 500% to about 1000% increase in continuous exercise power output (watts) at about $VO_2$ 62% for 90 minutes and not less than about a 25% increase in high intensity (Burst) exercise, about $VO_2$ 86%, power output and duration following 90 minutes of continuous exercise, and increase the number of effective "burst" periods by >100% as compared to performance when utilizing as performance enhancing drinks such as GATORADE, CYTOMAX, or POWERADE.

The measurement of cumulative power output potential is well known to one of skill in the art (see, e.g., Byrne, C.; Twist, C.; Eston, R. Neuromuscular function after exercise-induced muscle damage: theoretical and applied implications. *Sports Med.* 2004, 34, 49-69; Hunter, A.; St, C.;

Lambert, M. et al. Effects of supramaximal exercise on the electromyographic signal. *Br. J. Sports Med.* 2003, 37, 296-299; and Williams, S. G.; Cooke, G. A.; Wright, D. J. et al. Peak exercise cardiac power output: A direct indicator of cardiac function strongly predictive of prognosis in chronic heart failure. *Eur. Heart J.* 2001, 22, 1496-1503). In a particularly advantageous embodiment, the yo-yo-intermittent recovery test is utilized for measuring cumulative power output potential (see, e.g., Krustrup, P.; Mohr, M.; Amstrup, T. R. et al. The yo-yo intermittent recovery test: physiological response, reliability, and validity. *Med. Sci. Sports Exerc.* 2003, 35, 697-705).

In another preferred embodiment, consumption of the nutrient compositions results in an increased sustainability in concentration, hand/eye coordination etc. during extended exercise. Tests of this nature are known in the art and anyone or more can be utilized. See, for example, U.S. Pat. No. 7,300,365. This would translate into improved athletic performance but also aid promotion for non-athletic, academic and or work, performance uses.

In another preferred embodiment, consumption of the nutrient compositions results in improved concentration and brain function as compared to no supplemental carbohydrate (i.e. the nutrient compositions) ingestion.

In another preferred embodiment, consumption of the nutrient compositions is expected to result in improved and stabilized blood glucose concentration and is therefore a beneficial beverage or food alternative for individuals with diabetes.

In another preferred embodiment, the compositions are packaged for accessibility during longer periods of athletic exertion (e.g., a marathon) or when immediate energy and associated supplements are required, the product comprising the nutrients is in a solid or gel from which is wearable, yet protected, on the person in a ready to consume form.

In another preferred embodiment, the nutritional composition is packaged so that it is easily handled and stored in backpacks, duffel bags, pockets, etc. Preferably, the packaging is environmentally friendly.

In a preferred embodiment the nutritional compositions are admixed with a biodegradable binder or encapsulated within a biodegradable microsphere which allows for sustained release of desired carbohydrates and other nutrients. "Biodegradable", as defined herein, means the polymer will degrade or erode in vivo to form smaller chemical species. Degradation can result, for example, by enzymatic, chemical and/or physical processes. Suitable biocompatible, biodegradable polymers include, for example, polysaccharides, poly(lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and polyorthoester, biodegradable polyurethanes, hydrogels, blends and copolymers thereof.

Biocompatible, non-biodegradable polymers suitable for the methods and compositions of the present invention include non-biodegradable polymers selected from the group consisting of polyacrylates, polymethacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, hydrogels, blends and copolymers thereof.

In another preferred embodiment, hydrogels are used in the sustained release of the nutritional supplements. Physical polymeric hydrogels have been widely explored for biomaterials applications. Examples include hydrogels formed by complexation of enantiomeric polymer or polypeptide segments and hydrogels with temperature- or pH-sensitive properties. They attract special attention for sustained drug delivery because of the mild and aqueous conditions involved in trapping delicate bioactive agents such as proteins. For example, in situ formed hydrogels, formed from thermosensitive block copolymers, have also been proposed as sustained release matrices for drugs. They have the advantage that there is no chemical reaction involved in the gel formation. These copolymer hydrogels are usually designed for macromolecular drugs such as proteins and hormones. Preferably the polymer is in an aqueous solution, which forms a hydrogel. For example, suitable aqueous polymer solutions contain about 1% to about 80%, about 2% to about 75%, about 3% to about 70%, about 4% to about 65%, about 3% to about 70%, about 4% to about 65%, about 5% to about 60%, about 6% to about 55%, about 7% to about 50%, about 8% to about 45%, about 9% to about 42% polymer, preferably about 10% to about 40% polymer. Suitable hydrogels can also contain about 1% to about 20%, about 2% to about 19%, about 3% to about 18%, about 4% to about 17% cyclodextrin (w/w) (based on the weight of total solution), preferably about 5% to 15% cyclodextrin, to solubilize nutrients that have limited water solubility. The hydrogel is typically formed using an aqueous carrier fluid. For example, typical aqueous solutions contain about 1% to about 80%, about 2% to about 75%, about 3% to about 70%, about 4% to about 65%, about 3% to about 70%, about 4% to about 65%, about 5% to about 60%, about 6% to about 55%, about 7% to about 50%, about 8% to about 45%, about 9% to about 42% polymer, preferably about 10% to about 40% polymer.

The hydrogel composition may also contain a secondary polymer, which may complex with the nutrient, conjugate the nutrient, or both. The secondary polymer may suitably be a polyester, polyurethane, polyamide, polyether, polysaccharide, poly(amino acid), polypeptide, or a protein. Preferably the secondary polymer is a di- or mono-functional polymer or polyionic polymer with poly(ethylene glycol) segments. In the case where nutritional supplements conjugate or complex to the hydrogels, then the hydrogel formulations act not only as a matrix but also a carrier of the nutritional supplements. This means that the nutritional supplements, e.g. a variety of carbohydrates, are not only physically entrapped in the hydrogel, but also are complexed or conjugated to the molecules that form the hydrogel. A secondary polymer may also be used to alter the properties, such as porosity and viscosity, of the hydrogel matrix.

The properties of the hydrogels are tunable by using different polymer block molecular weights, by adjusting the cyclodextrin content, and through the use of secondary polymers. For example, the hydrogel may be adjusted to be a more flexible hydrogel or a more rigid hydrogel. The hydrogel structure can be tailored to have variable viscosity and longer or shorter drug release rates. The degree of hydrophobicity of the poly(hydroxyalkanoate) can also be selected for a desired sustained release rate.

The duration of extended release is dependent on the molecular weights of the block polymers, particularly the molecular weight of the hydrophobic poly(hydroxyalkanoate) section (e.g., PHB). The release rate may be altered in accordance with the invention to achieve a desired duration of response by selecting: a particular poly(hydroxyalkanoate); the stereo-isomeric state of the selected poly(hydroxyalkanoate); the molecular weight of the selected poly(hydroxyalkanoate); and the relative quantity of cyclodextrin used in the hydrogel, to achieve a desired duration and rate of sustained release. The molecular weight and selection of the hydrophilic poly(alkylene oxide) also impacts the sustained release kinetics, but to a lesser extent than the hydrophobic poly(hydroxyalkanoate) component. Secondary polymers may also be utilized to change the release kinetics. Hydrogels can provide sustained release over a period of one or more days by adjustment of the molecular weights of the block polymers and the copolymer, as well as the cyclodextrin content within the hydrogel of the present invention and the potential use of secondary polymers.

Microencapsulation of components of the nutritional supplement in biodegradable polymers such as polylactide-polyglycolide is also contemplated. Depending on the ratio of component to polymer, and the nature of the particular polymer employed, the rate of component release may be sustained. Examples of other biodegradable polymers include poly(orthoester)s and poly(anhydride)s. The formulations are also prepared by entrapping the component in liposomes or microemulsions which are compatible with body tissue.

Further, the terminal functionalities of a polymer can be modified. For example, polyesters may be blocked, unblocked or a blend of blocked and unblocked polymers. A blocked polyester is as classically defined in the art, specifically having blocked carboxyl end groups. Generally, the blocking group is derived from the initiator of the polymerization and is typically an alkyl group. An unblocked polyester is as classically defined in the art, specifically having free carboxyl end groups.

In an advantageous embodiment, blends of polysaccharides are utilized to synthesize aqueous dispersions of microparticles or nanonparticles. Advantageously, the polysaccharides are hydrophobically modified polysaccharides wherein the polysaccharides form interpenetrating polymer networks. In an especially advantageous embodiment, the polysaccharides contain carboxylic acid groups, such as, but not limited to, the polysaccharides of FIG. 1.

Without being bound by theory, it is expected that the carboxy containing hydrogel particles are in a collapsed state in the acidic environment of the stomach. Hence, the encapsulated sugar molecules are retained within the particles in the stomach. The hydrogel particles will achieve an expanded state when they reach the small intestine (pH 5-7), and will release the encapsulated sugar at a rate faster than that in the stomach. A key feature of the proposed polysaccharide hydrogels is their pH responsiveness. Ideally, the hydrogels should not swell in the acidic environment of the stomach, but should swell upon entry into the small intestine and release the encapsulated sugars at a controlled rate. Advantageously, the carbohydrates of the present invention are controlled release particles dispersed in an aqueous medium, but may also be stored in a solid particulate form.

In a particularly advantageous embodiment, the hydrogels comprise hydrophobized polysaccharides. Polysaccharides may be functionalized with hydrophobes such as cholesterol. For example, polysaccharides such as, but not limited to, pullulan, dextran and mannan may be partly substituted by various hydrophobic groups such as, but not limited to, long alkyl chains and cholesterol.

The nanoparticles or microparticles of the present invention may comprise modified starch molecules with grafted fatty acid moieties. The fatty acid may be grafted on to starch using potassium persulfate, for example, as a catalyst.

In another embodiment, the invention also encompasses surface-modification of nanoscale starch particles using, for example, stearic acid chloride (a hydrophobe), poly(ethylene glycol) or methyl ether (a hydrophilic molecule). In another embodiment, the modified starch may be an acryloyl-modified starch or an acryloyl-modified hydroxyethyl starch.

In an advantageous embodiment of the invention, the polysaccharide was first derivatized to introduce aldehydic or carboxylic groups on the side chain. These groups were then crosslinked to produce more stable three-dimensional networks.

In an advantageous embodiment, the particles are crosslinked to form hydrogels. Crosslinking may be performed using free radical initiators such as persulfate salts, or redox systems involving ascorbic acid, or a naturally occurring crosslinker such as genipin. Ionic crosslinking is also explored. Anionic polysaccharides such as gellan can be used for ionic crosslinking, instead of chemicals such as borax which may not be desirable in a food formulation.

The present invention further relates to the preparation of hydrogels. In an advantageous embodiment, a blend of hydrophobically modified polysaccharide such as, but not limited to, hydroxypropyl cellulose and a carboxy containing polysaccharide such as, but not limited to, alginate or carboxymethyl cellulose may be used to prepare the hydrogel particles of the present invention. The hydrophobically modified polysaccharide results in spontaneous particle formation due to phase separation in water, while the polysaccharide containing carboxylic acid groups imparts a pH-responsive behavior and will also increase intestinal transit time. In one embodiment, nanoparticle suspensions may be synthesized by self-assembly of chitosan and carboxymethyl cellulose hydrolysates. The polymers are hydrolyzed with the enzymes chitosanase and cellulase, respectively. Electrostatic interactions between the carboxylate groups of carboxymethyl cellulose with the amino groups of chitosan result in spontaneous formation of nanoparticles by mixing solutions of the two polymers. Particle size depended on the mixing ratio of the solutions, and also by the molecular weight of the polymers. It was necessary to hydrolyze the polymers and lower the molecular weight before mixing in order to prevent the formation of macroscopic gel.

In another embodiment, hydrogels may be prepared from mixtures of acidic polysaccharides such as, but not limited to, alginates, and basic polysaccharides such as, but not limited to, oligosaccharide derivatives of chitosan; a basic polysaccharide such as, but not limited to, chitosan and anionic polysaccharide such as, but not limited to, hyaluronic acid; alginate and oxidized alginate blended with chitosan; grafted agar and sodium alginate blend with acrylamide; gellan co-crosslinked with scleroglucan; photocrosslinked modified dextran; starch reacted with glycidyl methacrylate; or polymerizable saccharide monomers, such as sucrose, created by reaction of the sugar with epoxy acrylate, or methacryloyl chloride and acetyl chloride.

Figure 8A:
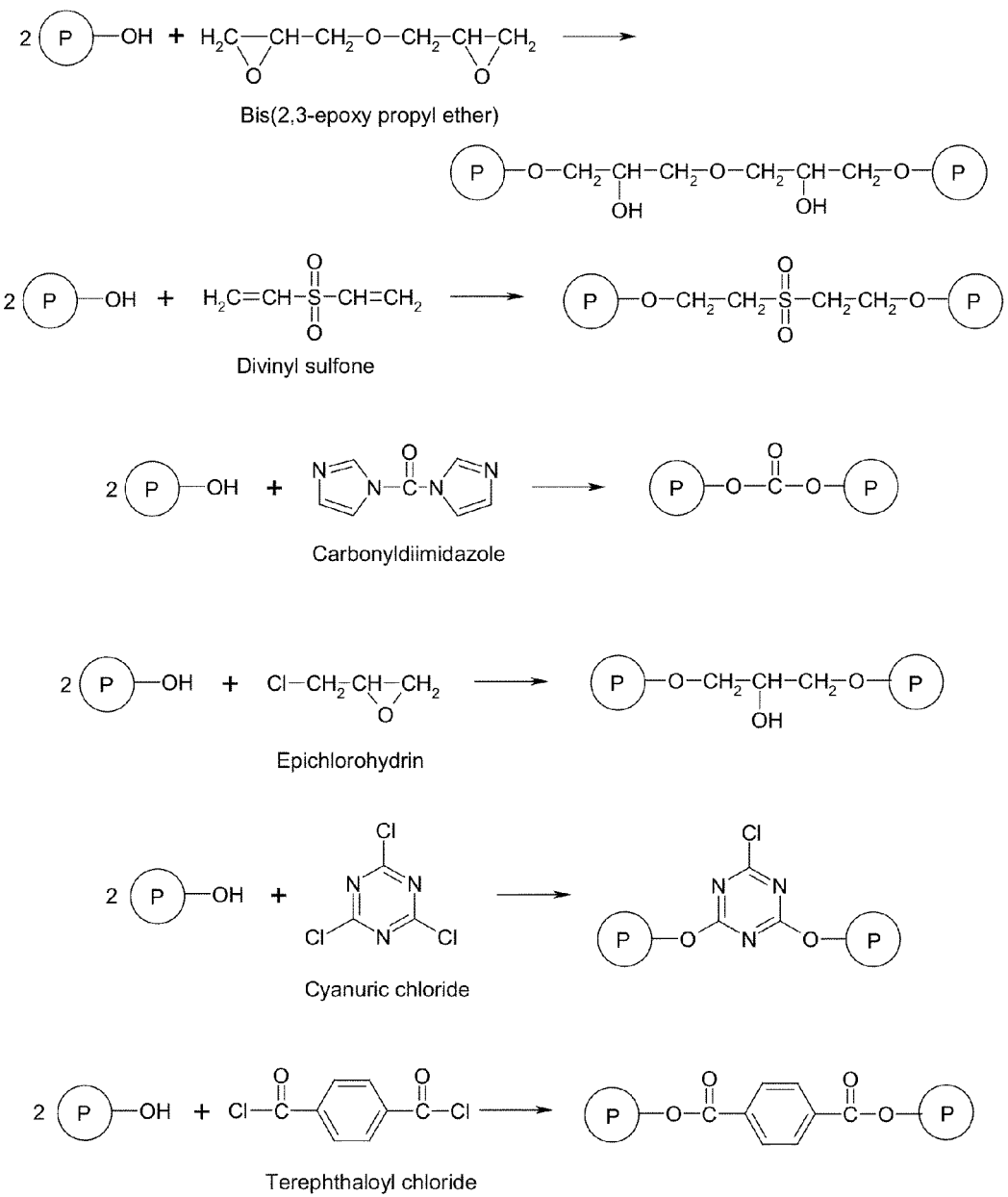
FIGS. 8A and 8B depict crosslinking of polysaccharides containing hydroxyl groups. P represents a polysaccharide segment.
Figure 8B:
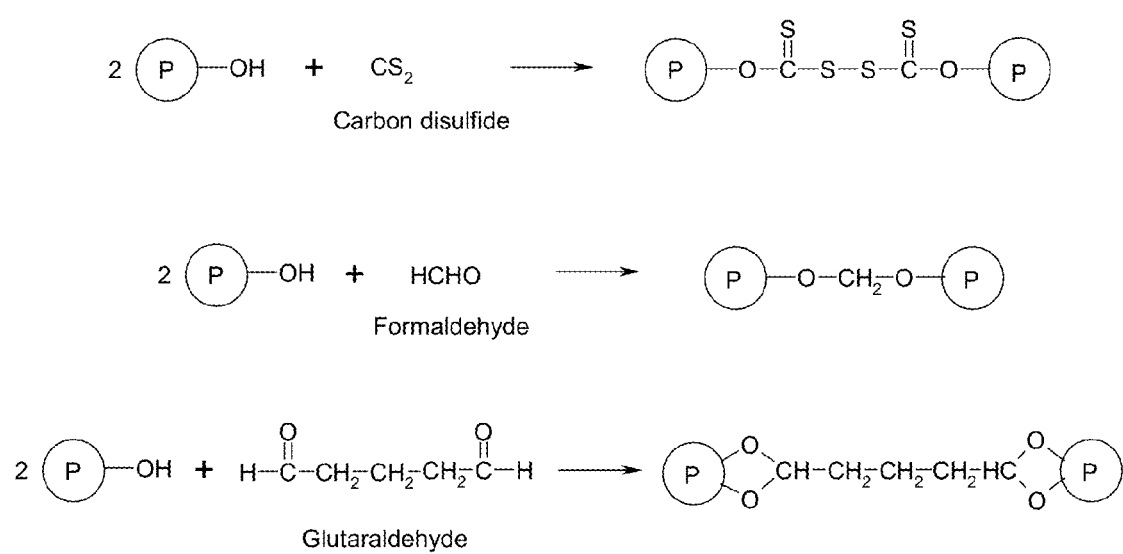
Figure 9:
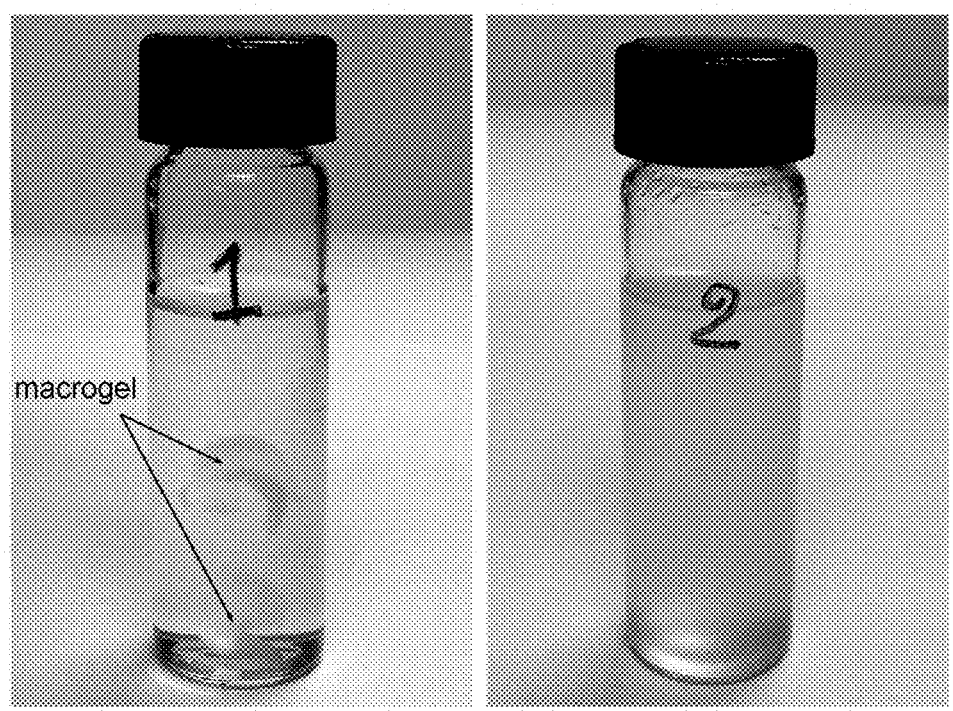
FIG. 9 depicts a crosslinked hydroxypropyl cellulose macrogel and a colloidally stable dispersion of hydroxypropyl cellulose microgel particles in water.

Crosslinking of polysaccharides containing hydroxyl groups, e.g. starch, hydroxyalkyl starch, hydroxyalkyl cellulose, etc., can be achieved using a variety of reagents including bis-epoxides, divinyl sulfone, N,N'-carbonyldiimidazole, cyanuric chloride, terephthaloyl chloride, carbon disulfide, formaldehyde, and glutaraldehyde as shown in FIGS. 8A and 8B [Park, H.; Park, K.; Shalaby, W. S. W. *Biodegradable Hydrogels for Drug Delivery*, Technomic Publishing Company: Lancaster, Pa., 1993]. Crosslinking to form macroscopic hydrogels may be readily achieved using these reagents. Kabra et al. [Kabra, B. G.; Gehrke, S. H.;

Spontak, R. J. Microporous, responsive hydroxypropyl cellulose gels. 1. Synthesis and microstructure. *Macromolecules* 1998, 31, 2166-2173] have used divinyl sulfone crosslinker to prepare macrogels of hydroxypropyl cellulose. The synthesis of hydrogel nano- or microparticles, on the other hand, requires careful selection of reaction conditions to prevent precipitation (due to colloidal instability) or macrogel formation. The difference between a macrogel and a colloidally-stable microgel suspension is evident from the photographs of two crosslinked samples of hydroxypropyl cellulose polymer, shown in FIG. 9. Both the vials shown in FIG. 9 contain about 4% (w/v) of hydroxypropyl cellulose in water. The vial labeled '1' shows a macrogel, while the vial labeled '2' contains a colloidally stable microgel suspension of hydroxypropyl cellulose To prevent macrogel formation and colloidal aggregation, the polysaccharide concentration has been kept fairly low (below about 1 wt %) in the crosslinking reactions. Cai et al. [Cai, T.; Hu, Z.; Marquez, M. Synthesis and self-assembly of nearly monodisperse nanoparticles of a naturally occurring polymer. *Langmuir* 2004, 20, 7355-7359] have prepared nanoparticles of crosslinked hydroxypropyl cellulose using divinyl sulfone crosslinker at 0.05 wt % polymer concentration. The toxicity of divinyl sulfone is of concern in synthesizing formulations for controlled release of nutrients. FIGS. 8A and 8B depict crosslinking of polysaccharides containing hydroxyl groups. P represents a polysaccharide segment.

The transport of small molecules such as glucose through polysaccharide hydrogels has been investigated for cell encapsulation and tissue engineering [McEntee, M.-K. E.; Bhatia, S. K.; Tao, L.; Roberts, S. C.; Bhatia, S. R. Tunable transport of glucose through ionically-crosslinked alginate gels: effect of alginate and calcium concentration. *J. Appl. Polym. Sci.* 2008, 107, 2956-2962]. Ionically-crosslinked alginate hydrogel beads, with an average bead diameter of 2 mm, were prepared using alginate and calcium chlorides. The researchers found a two-step release profile for glucose over a time range of 20-50 min. It should be noted that the release rates were measured by suspending the glucose-loaded spheres in pure water. The large difference in the concentration of glucose inside the sphere and the suspending fluid (pure water) resulted in a relatively rapid release of sugar (within about 50 min after suspension).

Covalent-crosslinking is expected to impart greater stability (against premature disintegration) to the hydrogel spheres, in the wide range of pH and ionic strength conditions that are encountered in the GI tract, than ionically-crosslinked hydrogels. When trisodium metaphosphate is used as the crosslinking agent, covalent-crosslinks are formed. The release rate of nutrients is tuned by controlling the crosslink density of the microspheres. More importantly, the release rate depends on the concentration of the nutrients outside the particles, in the aqueous phase of the suspension. Applicants' dispersions contain a relatively high sugar concentration in the aqueous phase. Diffusion of nutrients from the hydrogel microparticles occurs only when the nutrients get depleted from the aqueous phase. Hence, the particles act as reservoirs of sugar and supply nutrients within the intestinal lumen over a time period significantly beyond the duration reported in the study using ionically-crosslinked alginate beads (~50 min) [McEntee, M.-K. E.; Bhatia, S. K.; Tao, L.; Roberts, S. C.; Bhatia, S. R. Tunable transport of glucose through ionically-crosslinked alginate gels: effect of alginate and calcium concentration. *J. Appl. Polym. Sci.* 2008, 107, 2956-2962]. In Applicants' formulations, the nutrients dissolved in the aqueous phase will be initially absorbed across the intestinal ephithelium. The microparticles release entrapped nutrients at low rates initially (because of low concentration gradient), and at a faster rate when the aqueous phase nutrients are depleted (because of a greater concentration difference).

Acceptable molecular weights for polymers used in the present invention may be determined by a person of ordinary skill in the art accounting for factors such as the desired polymer degradation rate, physical properties such as mechanical strength and rate of dissolution of polymer in solvent. Typically, an acceptable range of molecular weights is of about 2,000 Daltons to about 2,000,000 Daltons, about 3,000 Daltons to about 1,900,000 Daltons, about 4,000 Daltons to about 1,800,000 Daltons, about 5,000 Daltons to about 1,700,000 Daltons, about 6,000 Daltons to about 1,600,000 Daltons, about 7,000 Daltons to about 1,500,000 Daltons, about 8,000 Daltons to about 1,400,000 Daltons, about 9,000 Daltons to about 1,300,000 Daltons, about 10,000 Daltons to about 1,200,000 Daltons, about 12,000 Daltons to about 1,100,000 Daltons, about 13,000 Daltons to about 1,000,000 Daltons, about 14,000 Daltons to about 900,000 Daltons, about 15,000 Daltons to about 800,000 Daltons, about 16,000 Daltons to about 700,000 Daltons, about 17,000 Daltons to about 600,000 Daltons, about 18,000 Daltons to about 500,000 Daltons, about 19,000 Daltons to about 400,000 Daltons, about 20,000 Daltons to about 300,000 Daltons, about 21,000 Daltons to about 200,000 Daltons, about 22,000 Daltons to about 100,000 Daltons, or about 23,000 Daltons to about 50,000 Daltons. In one embodiment, the polymer is a biodegradable polymer or copolymer.

In another preferred embodiment, the nutritional supplements can be encapsulated in microparticles or microspheres. These particles optionally comprise surfactants such as a cationic or anionic surfactant that is entrapped and fixed to the particle surface. The bioadhesive properties of the microparticles are attributed to the charged surfactants entrapped on the particle surface as the hydrophobic ends of the surfactants are embedded in the solid core and the hydrophilic ends are exposed on the surface of the microparticles.

Bioadhesive substances, also denoted mucoadhesive substances, are generally known to be materials that are capable of being bound to a biological membrane and retained on that membrane for an extended period of time. Compared with conventional controlled release systems, bioadhesive controlled release systems have the following advantages: i) a bioadhesive controlled release system localizes a biological active ingredient in a particular region, thereby improving and enhancing the bioavailability for active ingredients which may have poor bioavailability by themselves, ii) a bioadhesive controlled release system leads to a relatively strong interaction between a bioadhesive substance and a mucosa, such an interaction contributes to an increasing contact time between the controlled release system and the tissue in question and permits localization of the active released from the controlled release system to a specific site, iii) a bioadhesive controlled release system prolongs delivery of biological active ingredients in almost any non-parenteral route, iv) a bioadhesive controlled release system can be localized on a specific site with the purpose of local therapy, v) a bioadhesive controlled release system can be targeted to specific diseased tissues, and vi) a bioadhesive controlled release system is useful when conventional approaches are unsuitable, such as for certain biological active ingredients which are not adequately absorbed.

The microparticles can also include at least one co-surfactant. The co-surfactant can be a natural biologically compatible surfactant or a pharmaceutically acceptable non-natural surfactant. The co-surfactant assists in maintaining particles within the desired size range and preventing their aggregation. The co-surfactant comprises less than about 5%, less than about 4%, less than about 3%, less than about 2%, preferably less than about 1%, less than about 0.9%, less than about 0.8%, less than about 0.7%, less than about 0.6%, less than about 0.5%, less than about 0.4%, less than about 0.3%, less than about 0.2% and more preferably less than about 0.1% by weight of the particle.

The microparticles are preferably formed as an aqueous continuous phase suspending a colloidal phase of submicron particles. The aqueous continuous phase of the particle suspension can contain antioxidants, preservatives, microbicides, buffers, osmoticants, cryoprotectants, and other known pharmaceutically useful additives or solutes.

The microparticles sustain the release rate of nutritional supplements for an extended period of time. For example, the micro particles sustain the release of nutritional supplements for a period between about 1 minute and twelve hours.

The use of microparticles which provide varying rates of nutrient release are contemplated. For example, the kinetics of nutrient-release may be any of the following: (i) a steady-state or zero-order release rate in which there is a substantially uniform rate of release throughout; (ii) a first-order release rate in which the rate of release declines towards zero with time; and (iii) a delayed release in which the initial rate is slow, but then increases with time.

The term "bioadhesion" relates to the attachment of a material to a biological substrate such as a biological membrane. The term "mucoadhesive substance" is in accordance with the generally accepted terminology and is used synonymously with the term "a bioadhesive substance".

A cationic surfactant is incorporated on an outer surface of the microparticle to form a bioadhesive microparticle. The surfactant is entrapped and fixed to the particle surface and forms a coating at the interface surrounding the particle core. The interface surrounding the core is hydrophobic. The cationic surfactant also stabilizes the outer surface of the hydrophobic core component of the microparticles, thereby promoting a more uniform particle size.

Examples of surface active materials that are capable of strong bonding to the negatively charged and hydrophilic surfaces of tissues are preferable for use as cationic charged surfactants. Suitable surface active materials include straight-chain alkylammonium compounds, cyclic alkylammonium compounds, petroleum derived cationics, and polymeric cationic materials. Cetylpyridinium chloride was found to exhibit strong bioadhesive properties on biological surfaces, and is a preferred surface active material. The surfactant is present in a proportion of about 0.01% to about 5%, preferably about 0.05% to about 2%, by weight of the suspension.

Straight-chain alkylammonium compounds are cationic surface active materials in which one or more hydrophobic alkyl groups are linked to a cationic nitrogen atom. The linkage can also be more complex as, for example, in R—C(=O)—NHCH$_2$CH$_2$CH$_2$N(CH$_3$)$_2$. Alternatively, the cationic surface active material can contain more than one cationic nitrogen atom such as the class of compounds of R—NHCH$_2$CH$_2$CH$_2$NH$_2$ and derivatives thereof. Representative examples of suitable compounds for the cationic surfactant include, but are not limited to: cetyl trimethylammonium chloride (CTAB), hexadecyltrimethylammonium bromide (HDTAB), stearyl dimethylbenzylammonium chloride, lauryl dimethylbenzylammonium chloride, cetyl dimethylethylammonium halide, cetyl dimethylbenzylammonium halide, cetyl trimethylammonium halide, dodecyl ethyldimethylammonium halide, lauryl trimethylammonium halide, coconut alkyltrimethylammonium halide, and C8-C20 N,N-dialkyldimethylammonium halide.

Other suitable compounds for the cationic surfactant include, but are not limited to, bis(hydrogenated tallow alkyl)dimethylammonium chloride which is known to adsorb onto the surface with hydrophobic groups oriented away from it, 2-hydroxydodecyl-2-hydroxyethyl dimethyl ammonium chloride [CAS no. xx] and N-octadecyl-N,N', N'-tris-(2-hydroxyethyl)-1,3-diaminopropane dihydrofluoride [CAS no. 6818-37-7].

Surface-active quaternary ammonium compounds in which the nitrogen atom carrying the cationic charge is part of a heterocyclic ring can be used as the cationic surfactant. Examples of suitable compounds are laurylpyridinium chloride, bromide laurylpyridinium, tetradecylpyridinium bromide, and cetylpyridinium halide where the halide is selected from chloride, bromide or fluoride.

Polymeric amines which can be used as the cationic surfactant comprise a class of polymers containing ionic groups along the backbone chain and exhibit properties of both electrolytes and polymers. These materials contain nitrogen, of primary, secondary, tertiary or quaternary functionality in their backbone and may have weight average molecular weights as low as about 100 or higher than about 100,000. Suitable polymeric amines useful as a cationic surfactant include, but are not limited to, polydimeryl polyamine available from General Mills Chemical Co., polyamide, polyacrylamides, polydiallyldimethylammonium chloride, polyhexamethylene biguanide compounds, and also other biguanides, for example those disclosed in U.S. Pat. Nos. 2,684,924, 2,990,425, 3,183,230, 3,468,898, 4,022,834, 4,053,636 and 4,198,425, herein incorporated by reference into this application, 1,5-dimethyl-1,5-diazaundecamethylene polymethobromide, such as "Polybrene" manufactured by Aldrich, polyvinylpyrrolidone and their derivatives, polypeptides, poly(allylamine) hydrochloride, polyoxyethylenated amines, and polyethyleneimine, such as "Polymin" manufactured by BASF.

Suitable polymeric materials for the cationic surfactant also include surface active cationic polymers prepared by converting a fraction of the amino groups to their acyl derivatives. For example, the polyethyleneimine is first condensed with less than the stoichiometric quantity of acid halides thus alkylating some of the amino groups and the remaining amino groups are then condensed with hydrogen halides such as hydrogen chloride or, preferably, hydrogen fluoride. The surface activity of these compounds varies with the number of amino groups which are acylated and with the chain length of the acylating group RCO. The condensation reaction can be performed with stearic or oleic acid chlorides in the presence of a solvent containing metal fluoride, preferably silver fluoride, in such a manner that metal chloride formed in the reaction precipitates from the solvent.

Also suitable, for the purpose of this invention, are cationic derivatives of polysaccharides such as dextran, starch or cellulose, for example, diethylaminoethyl cellulose. Examples of applicable copolymers based on acrylamide and a cationic monomer are available from Hercules Inc. under the trade name RETEN including RETEN 220, or from National Adhesives under the trade name FLOC AID including FLOC AID 305. Other useful acrylamide-based polyelectrolytes are available from Allied Colloids under the trade name PERCOL. Further examples of suitable materials are cationic guar derivatives such as those sold under the trade name JAGUAR by Celanese-Hall.

In another preferred embodiment, the microparticles comprise a hydrophobic core which is preferably formed of a biodegradable hydrophobic materials having barrier properties. Suitable, nontoxic, pharmaceutical solid core materials are inert hydrophobic biocompatible materials with a melting range between about 50° C. and about 120° C., between about 60° C. and about 110° C., between about 70° C. and about 100° C. or between about 80° C. and about 90° C. Examples include, but are not limited to, natural, regenerated, or synthetic waxes including: animal waxes, such as beeswax; lanolin and shellac wax; vegetable waxes such as carnauba, candelilla, sugar cane, rice bran, and bayberry wax; mineral waxes such as petroleum waxes including paraffin and microcrystalline wax; cholesterol; fatty acid esters such as ethyl stearate, isopropyl myristate, and isopropyl palmitate; high molecular weight fatty alcohols such as cetostearyl alcohol, cetyl alcohol, stearyl alcohol, and oleyl alcohol; solid hydrogenated castor and vegetable oils; hard paraffins; hard fats; biodegradable polymers such as polycaprolactone, polyamides, polyanhydrides, polycarbonates, polyorthoesters, polylactic acids, and copolymers of lactic acid and glycolic acid; cellulose derivatives and mixtures thereof. Other hydrophobic compounds which may be used in the present invention include triglycerides, preferably of food grade purity or better, which may be produced by synthesis or by isolation from natural sources. Natural sources may include animal fat or vegetable oil, such as, soy oil, a source of long chain triglycerides (LCT). Other suitable triglycerides are composed predominantly of medium length fatty acids (C10-C18), denoted medium chain triglycerides (MCT). The fatty acid moieties of such triglycerides can be unsaturated, monounsaturated or polyunsaturated. Mixtures of triglycerides having various fatty acid moieties are also useful for the present invention. The core can comprise a single hydrophobic compound or a mixture of hydrophobic compounds. Hydrophobic materials are known to those skilled in the art and are commercially available, as described in the list of suitable carrier materials in Martindale, *The Extra Pharmacopoeia*, $28^{th}$ ed.; The Pharmaceutical Press: London, 1982; pp 1063-1072. Considerations in the selection of the core material include good barrier properties to the active ingredients and sensory markers, low toxicity and irritancy, biocompatibility, stability, and high loading capacity for the active ingredients of interest.

An amphiphilic or nonionic co-surfactant can be used in the microparticles of the present invention to provide improved stability. Co-surfactants can be formed of natural compounds or normatural compounds. Examples of natural compounds are phospholipids and cholates. Examples of normatural compounds include: polysorbates, which are fatty acid esters of polyethoxylated sorbitol sold by Unigema surfactants as Tween; polyethylene glycol esters of fatty acids from sources such as castor oil; polyethoxylated fatty acid, such as stearic acid; polyethoxylated isooctylphenol/formaldehyde polymer; poloxamers, such as, poly(oxyethylene)poly(oxypropylene) block copolymers available from BASF as Pluronic; polyoxyethylene fatty alcohol ethers available from ICI surfactants as Brij; polyoxyethylene nonylphenyl ethers sold by Union Carbide as Triton N; polyoxyethylene isooctylphenyl ethers sold by Union Carbide as Triton X; and SDS. Mixtures of surfactant molecules, including mixtures of surfactants of different chemical types, can be used in the present invention. Surfactants preferably are suitable for pharmaceutical administration and compatible with the drug to be delivered.

Particularly suitable surfactants include phospholipids, which are highly biocompatible. Especially preferred phospholipids are phosphatidylcholines (lecithins), such as soy or egg lecithin. Other suitable phospholipids include phosphatidylglycerol, phosphatidylinositol, phosphatidylserine, phosphatidic acid, cardiolipin, and phosphatidylethanolamine. The phospholipids may be isolated from natural sources or prepared by synthesis. Phospholipid surfactants are believed to usually form a single monolayer coating of the hydrophobic core. The co-surfactant can be present in an amount less than about 5%, preferably less than about 1%, and more preferably less than about 0.1%, relative to the weight of hydrophobic core component. In some embodiments, one or more co-surfactants can be used.

In another preferred embodiment, the nutritional supplements comprise compounds which modulate uptake of carbohydrates. In the gastrointestinal tract, chromium and vanadium (either individually, or preferably in concert) modulate sugar transport (e.g., glucose transport) by typically slowing glucose absorption. Slower glucose absorption slows insulin release and reduces excessive insulin responses in response to rising blood glucose levels after a meal. This benefits pancreatic secretion of insulin by reducing both the glucose load and rate of glucose load over the initial phases of glucose detection, absorption and metabolism by the body. Reduced rates of glucose loading reduce the stress on beta cells normally associated with the insulin response to rising glucose. Moreover, slower or modulated glucose absorption permits more time for insulin to stimulate normal sugar metabolic routes either before glucose loading is complete, or during a slower rate of glucose loading. Consequently, insulin dependent mechanisms have more time to prepare for the arrival of sugars from the intestine. This modulation of glucose absorption improves short-term insulin modulation in the liver, muscle, and adipose tissue. These effects in the gastrointestinal tract are, in all likelihood, short-term responses, and they are not necessarily associated with the longer-term systemic effects of chromium and vanadium administration.

In addition, chromium and vanadium may potentially slow glucose metabolism by interacting with the intestine, particularly the epithelium of the intestine responsible for sugar metabolism (including absorption). One primary mechanism for sugar transport in the gut is sodium facilitated sugar transport. Such transporters are located in the lumenal membrane of the epithelium. The basolateral membrane may also have an additional sugar transporter that facilitates transport out the cell and into the blood. For net sugar absorption from the lumen of the gut to the blood, sodium facilitated sugar transport generally requires a sodium concentration favorable to the diffusion of sodium into the epithelium cell from the lumen. This concentration gradient is largely generated by the active transport of the Na/K ATPase in the epithelium cells, which generally transports three sodium atoms out of the cell to the blood side of the epithelium in exchange for two sodium atoms in the reverse direction.

Each cycle of the pump requires hydrolysis of one ATP to transport sodium and potassium against their respective concentration gradients. The hydrolysis reaction requires a divalent cation, typically magnesium. In many instances, however other divalent cations may substitute or enter into the hydrolysis reaction with varying degrees of catalytic activity or inhibition. Substitution of trivalent cations for divalent cations in the cycle generally leads to significant inhibition of the pumping activity and/or dephosphorylation from the phosphoenzyme intermediate state. Chromium may thus inhibit the Na/K ATPase activity by substituting for magnesium and thereby inhibiting, relative to magnesium, catalytic and transport activity, giving rise to a decreased sodium gradient across the lumenal membrane. The reduced gradient effects sugar transport by reducing the thermodynamic and kinetic forces favoring sugar entry from the gut.

In addition, during the hydrolysis of ATP in the catalytic cycle of the Na/K ATPase, a phosphoenzyme intermediate (EP) is formed between phosphate and an aspartic acid at the active site of APTase. This covalent EP is transient and is chemically distinct from phosphorylated proteins associated with kinases and phosphatases, which have also been shown to be affected by vanadium. Formation of EP in the catalytic cycle for Na/K ATPase is inhibited by vanadate present at low concentrations of less than 1 micromolar. Vanadate binds to the active site as a transition state analog of phosphate in a vanadyl-enzyme, or EV complex, rather than EP. The EV complex is highly stable, as the kinetics of loss of vanadate from the EV complex is relatively slow. Vanadate may thus effectively inhibit the Na/K ATPase by disrupting catalysis, through the formation of EV, giving rise to a decreased sodium gradient across the lumenal membrane. Consequently, the reduced gradient reduces sugar entry from the intestine.

Chromium and vanadium also operate at the systemic level after absorption of the two transition metals from the gut. Major sites of activity include the liver, muscle and adipose tissue. Vanadium may have particular activity with respect to phosphorylation systems, including the many phosphorylated proteins responsible for modulating metabolism. Chromium may also modulate metabolism at the cellular level. These systemic effects generally improve the action of insulin and/or metabolic pathways associated with sugar and/or lipid metabolism.

In regard to absorption and metabolism of the subject compositions, and the different components thereof, features of the alimentary tract may affect how compositions of the present invention, and methods of using the same, are utilized when ingested orally. The elements of the alimentary tract, including the gastrointestinal tract, may affect the dosage required for any such modality. Such features are well known to those of skill in the art.

In another preferred embodiment, the nutritional compositions are formulated into unit dosage forms such as tablets, caplets, powder, granules, beads, chewable lozenges, capsules, liquids, aqueous suspensions or solutions or similar dosage forms, using conventional equipment and techniques known in the art. Such formulations typically include a solid, semisolid, or liquid carrier. Exemplar carriers include lactose, dextrose, sucrose, sorbitol, mannitol, sutarches, gum acacia, calcium phosphate, mineral oil, cocoa butter, oil of theobroma, alginates, tragacanth, gelatin syrup, methyl cellulose, polyoxyethylene sorbitan monolaurate, methyl hydroxybenzoate, propyl hydroxybenzoate, talc, magnesium stearate, and the like.

Other formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a supplement or components thereof as an active ingredient. A supplement or components thereof may also be administered as a bolus, electuary, or paste.

In other formulations, the nutritional supplements are provided in beverages. The beverages of this invention can be carbonated beverages e.g., flavored seltzer waters, soft drinks or mineral drinks, as well as non-carbonated juices, punches and concentrated forms of these beverages. Beverages, especially juice and cola beverages, which are carbonated in the manner of soft drinks, as well as "still" beverages and nectars and full-strength beverages or beverage concentrates which contain at least about 45% by weight of juice are also contemplated.

By way of example, the fruit juices and fruit flavors used here in include grape, pear, passion fruit, pineapple, banana or banana puree, apricot, orange, lemon, grapefruit, apple, cranberry, tomato, mango, papaya, lime, tangerine, cherry, raspberry, carrot and mixtures thereof. Additionally, artificial flavors, e.g. cola, or natural flavors derived from these juices can be used in the beverages. Chocolate flavors and other non-fruit flavors can also be used to make beverages containing the vitamin and mineral supplement. Additionally, milk, obtained from cows or synthetic, is a contemplated beverage to which the powder compositions of this invention can be added. The milk may itself include other beverage components, in particular flavors such as chocolate, coffee, or strawberry. As used herein, the term "juice product" refers to both fruit and vegetable juice beverages and fruit and vegetable juice concentrates which comprise at least about 45% fruit juice. Vegetable when used herein includes both nonfruit edible plant parts such as tubers, leaves, rinds, and also if not otherwise indicated, any grains, nuts, beans, and sprouts which are provided as juices or beverage flavorings.

In one preferred embodiment, sport beverages can be supplemented by the powder compositions of the present invention. Typical sport beverages contain water, sucrose syrup, glucose-fructose syrup, and natural or artificial flavors. These beverages can also contain citric acid, sodium citrate, monopotassium phosphate, as well as other materials which are useful in replenishing electrolytes lost during perspiration.

Tables 2 and 3 depict components of representative sports and energy drink products.

TABLE 2

Representative energy drink products. The 'x' indicates that an unspecified amount of the ingredient is present in the formulation.

|  | Monster Energy | Red Bull | RockStar |
|---|---|---|---|
| Container Size | 16 oz | 8.3 oz | 8, 16, or 24 oz |
| Serving size | 8 oz | 8.3 oz | 8 oz |
| Vitamin B2 | 1.7 mg |  | 3.4 mg |
| Vitamin B3 | 20 mg | 100 mg | 20 mg |
| Vitamin B5 |  |  | 10 mg |
| Vitamin B6 | 2 mg | 125 mg | 2 mg |
| Vitamin B12 | 6 µg | 240 µg | 6 µg |
| Sodium | 180 mg | 200 mg | 40 mg |
| Potassium |  |  |  |
| Folic acid |  |  |  |
| Magnesium |  |  |  |
| Zinc |  |  |  |
| Taurine | 1000 mg |  | 1000 mg |
| Penax Ginseng extract | 200 mg |  | 25 mg |
| Energy Blend | 2500 mg |  | 1350 mg |
| L-Carnitine | x |  | 25 mg |
| Glucose | x |  |  |
| Caffiene | x | x | 80 mg |
| Guarana | x |  | 25 mg |

TABLE 2-continued

Representative energy drink products. The 'x' indicates that an unspecified amount of the ingredient is present in the formulation.

|  | Monster Energy | Red Bull | RockStar |
|---|---|---|---|
| Inositol | x |  | 25 mg |
| Glucuronolactone | x |  |  |
| Maltodextrin | x |  |  |
| Ginko biloba extr |  |  | 150 mg |
| Milk thistle |  |  | 20 mg |
| *Muira pauma* extract |  |  |  |
| Catuaba extract |  |  |  |
| Epimedium extract |  |  |  |
| Yerba mate extract |  |  |  |
| Ingredients |  |  |  |
| Water |  |  |  |
| Carbonated water | x | x | x |
| Sucrose | x | x | x |
| Fructose |  |  |  |
| Fructose-glucose syrup |  |  |  |
| Glucose | x | x | x |
| Acelsulfame |  | x |  |
| Aspartame/Sucralose | x | x |  |
| Trehalose |  |  |  |
| Whey-protein isolate |  |  |  |
| Citric acid | x |  | x |
| Phoshoric acid |  |  |  |
| Lactic acid |  |  |  |
| Magnesium carbonate |  |  |  |
| Vitamin E acetate |  |  |  |
| Salt | x |  |  |
| Monopotassium phosphate |  |  |  |
| Ester gum |  |  |  |
| Sodium ascorbate |  |  |  |
| Sodium citrate | x | x | x |
| Flavor | x | x | x |
| Benzoic acid | x |  | x |
| Sorbic acid | x |  | x |
| Ascorbic acid | x |  |  |
| L-Carnitine | x |  | x |
| Niacinamide | x | x | x |
| Calcium pantothenate |  | x | x |
| Pantothenic acid |  |  |  |
| Calcium disodium |  |  |  |
| Pyroxidine hydrochloride | x | x |  |
| Magnesium lactate |  |  |  |
| Calcium lactate |  |  |  |
| Gum *acacia* |  |  |  |
| Cyanocobalamin | x | x |  |
| Potassium citrate |  |  |  |
| Modified food starch |  |  |  |
| Hibiscus extract |  |  |  |
| Calcium phosphate |  |  |  |
| Gum Arabic |  |  |  |
| Vanocobalamin |  |  |  |
| Red clover flower extract |  |  |  |
| Magnesium oxide |  |  |  |
| Zinc picolinate |  |  |  |
| *Muira pauma* extr |  |  |  |
| *Epimedium sagittatum* extract |  |  |  |
| Guarana seed extract | x |  |  |
| Yerba mate extract |  |  |  |
| Catuaba extract |  |  |  |
| Folic acid |  |  |  |
| Taurine | x | x |  |
| Penax Ginseng extract | x |  |  |
| Glucuronolactone | x | x |  |
| Inositol | x | x |  |
| Riboflavin | x |  |  |
| Maltodextrin | x |  |  |

TABLE 3

Representative sports drink products

|  | Gatorade | Accelerade | Propel Fit Water | Vitamin Water Revive | Life Water (Goji Melon) | Function: Alternative Energy |
|---|---|---|---|---|---|---|
| Container Size | 20 oz | 20 oz | 18.9 oz | 20 oz | 20 oz | 16.9 oz |
| Serving size | 8 oz | 8 oz | 8 oz | 8 oz | 8 oz | 8 oz |
| Vitamin B2 |  |  |  |  |  |  |
| Vitamin B3 |  |  |  | 20 mg |  | 10 mg |
| Vitamin B5 |  |  |  | 20 mg |  |  |
| Vitamin B6 |  |  | 12.5 mg | 12.5 mg | 5 mg | 1 mg |
| Vitamin B12 |  |  | 75 µg | 60 µg | 30 µg | 3 µg |
| Sodium | 110 mg | 120 mg | 35 mg |  | 20 mg | 120 mg |
| Potassium | 30 mg | 15 mg |  | 140 mg |  |  |
| Folic acid |  |  |  |  |  | 200 µg |
| Magnesium |  |  |  |  |  | 20 mg |
| Zinc |  |  |  |  |  | 4.95 mg |
| Taurine |  |  |  |  |  |  |
| Penax Ginseng extract |  |  |  |  |  |  |
| Energy Blend |  |  |  |  |  | 300 mg |
| L-Carnitine |  |  |  |  |  |  |
| Glucose |  |  |  |  |  |  |
| Caffiene |  |  |  |  |  | x |
| Guarana |  |  |  |  |  | x |
| Inositol |  |  |  |  |  |  |
| Glucuronolactone |  |  |  |  |  |  |
| Maltodextrin |  |  |  |  |  |  |
| *Ginko biloba* extract |  |  |  |  |  |  |
| Milk thistle |  |  |  |  |  |  |
| Muira pauma extract |  |  |  |  |  | x |
| Catuaba extract |  |  |  |  |  | x |
| *Epimedium* extract |  |  |  |  |  | x |
| Yerba mate extract |  |  |  |  |  | x |

TABLE 3-continued

Representative sports drink products

| | Gatorade | Accelerade | Propel Fit Water | Vitamin Water Revive | Life Water (Goji Melon) | Function: Alternative Energy |
|---|---|---|---|---|---|---|
| Ingredients | | | | | | |
| Water | x | x | x | x | x | x |
| Carbonated water | | | | | | |
| Sucrose | x | x | x | x | x | x |
| Fructose | | | | x | | |
| Fructose-glucose syrup | x | | | | | |
| Glucose | | | | | | |
| Acelsulfame | | | x | | | |
| Aspartame/sucralose | | | x | | | |
| Trehalose | | x | | | | |
| Whey-protein isolate | | x | | | | |
| Citric acid | x | x | x | x | x | x |
| Phoshoric acid | | x | | | | |
| Lactic acid | | x | | | | |
| Magnesium carbonate | | x | | | | |
| Vitamin E acetate | | x | 10% RDA | | x | |
| Salt | x | x | | | | x |
| Ester gum | x | x | | x | | |
| Sodium ascorbate | | x | | | | |
| Sodium citrate | x | | x | | | x |
| Flavor | x | x | x | x | x | x |
| Benzoic acid | | | | | | |
| Sorbic acid | | | | | | |
| Ascorbic acid | | | | x | x | x |
| L-Carnitine | | | | | | |
| Niacinamide | | | x | x | x | x |
| Calcium pantothenate | | | x | | x | |
| Pantothenic acid | | | | x | | |
| Calcium disodium | | | x | | | |
| Pyroxidine hydrochloride | | | x | x | x | x |
| Magnesium lactate | | | | | | |
| Calcium lactate | | | | | x | |
| Gum acacia | | | | x | | |
| Cyanocobalamin | | | | x | | x |
| Potassium citrate | | | | | x | |
| Modified food starch | | | | | x | |
| Hibiscus extract | | | | | x | |
| Calcium phosphate | | | | | x | |
| Gum Arabic | | | | | x | |
| Vanocobalamin | | | | | x | |
| Red clover flower extract | | | | | x | |
| Magnesium oxide | | | | | | x |
| Zinc picolinate | | | | | | x |
| Muira pauma extract | | | | | | x |
| Guarana seed extract | | | | | | x |
| Yerba mate extract | | | | | | x |
| Catuaba extract | | | | | | x |
| Folic acid | | | | | | x |
| Taurine | | | | | | |
| Penax Ginseng extr. | | | | | | |
| Glucuronolactone | | | | | | |
| Inositol | | | | | | |
| Riboflavin | | | | | | |
| Maltodextrin | | | | | | |

As used herein, the term "juice beverage" refers to a fruit or vegetable juice product which is in a single-strength, ready-to-serve, drinkable form. Juice beverages of the present invention can be of the "full-strength" type which typically comprise at least about 95% juice. Full strength juice beverages also include those products of 100% juice such as, for example, orange, lemon, apple, raspberry, cherry, apricot, pear, grapefruit, grape, lime, tangerine, carrot, pineapple, melon, mango, papaya, passion fruit, banana and banana puree, cranberry, tomato, carrot, cabbage, celery, cucumber, spinach, and various mixtures thereof. Juice beverages also include extended juice products which are referred to as "nectars". These extended juice products typically comprise from about 50% to about 90%, about 55% to about 85%, about 60% to about 80%, about 65% to about 75% juice, preferably, from about 50% to about 70% juice. Nectars usually have added sugars or artificial sweeteners or carbohydrate substitutes. As used herein, the term "citrus juice" refers to fruit juices selected from orange juice, lemon juice, lime juice, grapefruit juice, tangerine juice and mixtures thereof.

As used herein, the term "juice materials" refers to concentrated fruit or vegetable juice, plus other juice materials such as juice aroma and flavor volatiles, peel oils, and pulp or pomace. As used herein, the term "juice concentrate" refers to a fruit or vegetable juice product which, when diluted with the appropriate amount of water, forms drinkable juice beverages. Juice concentrates within the scope of the present invention are typically formulated to provide drinkable beverages when diluted with 3 to 5 parts by weight water.

As used herein the term "beverage concentrate" or "bottling syrup" refers to a mixture of flavors, water and from about 10% to about 60%, about 20% to about 50% or about 30% to about 40% sugar or carbohydrate substitute, i.e. sucrose, dextrose, corn syrup solids, fructose, dextrins, polydextrose and mixtures thereof.

The flavor component of the beverages and beverage concentrates contains flavors selected from fruit flavors, vegetable flavors, botanical flavors and mixtures thereof. As used herein, the term "fruit flavor" refers to those flavors derived from the edible reproductive part of a seed plant, especially one having a sweet pulp associated with the seed, and "vegetable flavor" refers to flavors derived from other edible parts of seed and other plants. Also included within the term "fruit flavor" and "vegetable flavor" are synthetically prepared flavors made to simulate fruit or vegetable flavors derived from natural sources. Particularly preferred fruit flavors are the citrus flavors including orange, lemon, lime and grapefruit flavors. Besides citrus flavors, a variety of other fruit flavors can be used such as apple, grape, cherry, pineapple, mango and papaya flavors and the like. These fruit flavors can be derived from natural sources such as juices and flavor oils, or can be synthetically prepared. As used herein, the term "botanical flavor" refers to flavors derived from parts of a plant other than the fruit; i.e. derived from nuts, bark, roots and leaves, and beans such as coffee, cocoa, and vanilla. Also included within the term "botanical flavor" are synthetically prepared flavors made to simulate botanical flavors derived from natural sources. Examples of such flavors include cola, tea, coffee, chocolate, vanilla, almond, and the like. Botanical flavors can be derived from natural sources such as essential oils and extracts, or can be synthetically prepared.

The flavor component can comprise a blend of various flavors, e.g. lemon and lime flavors, cola flavors and citrus flavors to form cola flavors, etc. If desired, juices such as orange, lemon, lime, apple, grape, carrot, celery, and like juices can be used in the flavor component. The flavors in the flavor component are sometimes formed into emulsion droplets which are then dispersed in the beverage concentrate. Because these droplets usually have a specific gravity less than that of water and would therefore form a separate phase, weighting agents (which can also act as clouding agents) are typically used to keep the emulsion droplets dispersed in the beverage. Examples of such weighting agents are brominated vegetable oils (BVO) and rosin esters, in particular the ester gums. See Green, L. F. *Developments in Soft Drinks Technology*; Applied Science Publishers: London, 1978; Vol. 1, pp 87-93, for a further description of the use of weighting and clouding agents in liquid beverages. Besides weighting agents, emulsifiers and emulsion stabilizers can be used to stabilize the emulsion droplets. Examples of such emulsifiers and emulsion stabilizers include the gums, pectins, celluloses, polysorbates, sorbitan esters and propylene glycol alginates. See Green, L. F. supra at p. 92. The particular amount of the flavor component effective for imparting flavor characteristics to the beverages and beverage concentrates ("flavor enhancing") can depend upon the flavor(s) selected, the flavor impression desired, and the form of the flavor component.

The flavor component can comprise at least 0.05% by weight of the beverage composition, and typically from 0.1% to 2% by weight for carbonated beverages. When juices are used as the flavor, the flavor component can comprise, on a single-strength basis, up to 25% fruit juice by weight of the beverage, preferably from 5% to 15% juice by weight for carbonated beverages.

Carbon dioxide can be introduced into the water which is mixed with the beverage syrup or into the drinkable beverage after dilution to achieve carbonation. The carbonated beverage can be placed into a container such as a bottle or can and then sealed. Any conventional carbonation methodology can be used to make the carbonated beverages of this invention. The amount of carbon dioxide introduced into the beverage will depend upon the particular flavor system used and the amount of carbonation desired. Usually, carbonated beverages of the present invention contain from 1.0 to 4.5 volumes of carbon dioxide. The preferred carbonated beverages contain from 2 to about 3.5 volumes of carbon dioxide.

The present invention is also particularly suited for the supplementation of beverages and beverage concentrates, including water and citrus juices. The beverages can contain from 3% to 100% juice or from about 0.05% to about 10% of an artificial or natural flavor, particularly orange juice. The concentrated orange juice, orange juice aroma and flavor volatiles, pulp and peel oils used in the method of the present invention can be obtained from standard orange juice. See Nagy, S.; Shaw, P. E.; Veldhuis, M. K. *Citrus Science and Technology*; AVI Publishing: Westport, Conn., 1977; Vol. 2, pp 177-252 for standard processing of oranges, grapefruit and tangerines. (See also Nelson et al. *Fruit and Vegetable Juice Processing Technology,* 3rd ed.; AVI Publishing: Westport, Conn., 1980; pp. 180-505, for standard processing of noncitrus juices such as apple, grape, pineapple, etc. to provide sources of juice and juice materials for noncitrus juice products).

Juices from different sources are frequently blended to adjust the sugar to acid ratio of the juice. Different varieties of oranges can be blended or different juices can be blended to get the desired flavor and sugar to acid ratio. A sugar to acid ratio of from about 8:1 to about 20:1 is considered acceptable for fruit juices. However, preferred sugar to acid ratios are typically from about 11:1 to about 15:1, especially for citrus juices. Sweeteners include the sugars normally present in juice products, for example glucose, sucrose, and fructose. Sugars also include high fructose corn syrup, invert syrup, sugar alcohols, including sorbitol, refiners syrup, and mixtures thereof. In addition to sugar, extended juice beverages of the present invention can contain other sweeteners. Other suitable sweeteners include saccharin, cyclamates, acetosulfam, L-aspartyl-L-phenylalanine lower alkyl ester sweeteners (e.g. aspartame). A preferred sweetener for use in such extended juice products is aspartame. For single-strength juice beverages, the sugar content can range from about 2° to about 16° Brix (16° Brix means the juice contains about 16% soluble solid, and so on). Typically, the sugar content of such beverages depends upon the amount of juice contained herein.

In solid dosage forms for oral administration (capsules, tablets, pills, dragees, powders, granules and the like), the supplement or components thereof is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the supplement or components thereof moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Tablets and other solid dosage forms may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which may be dissolved in sterile water, or sonic other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which may be used include polymeric substances and waxes. The active ingredient may also be in micro-encapsulated form, if appropriate, with one or more of the above-described nutritional supplements.

Liquid dosage forms for oral administration include pharmaceutically acceptable emulsions, microemulsions, solutions, suspensions, syrups and elixirs. In addition to the supplement or component, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions may also include adjuvants such as wetting agents, emulsifying and suspending agents, sweetening, flavoring, coloring, perfuming and preservative agents. Suspensions, in addition to the supplement or components thereof, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The composition of the invention can be administered as a capsule or tablet containing a single or divided dose of the inhibitor. Preferably, the composition is administered as a sterile solution, suspension, or emulsion, in a single or divided dose. Tablets may contain carriers such as lactose and corn starch, and/or lubricating agents such as magnesium stearate. Capsules may contain diluents including lactose and dried corn starch.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Molded tablets may be made by molding in a suitable machine, a mixture of the powdered active ingredient and a suitable carrier moistened with an inert liquid diluent.

When preparing dosage form incorporating the compositions of the invention, the compounds may also be blended with conventional excipients such as binders, including gelatin, pregelatinized starch, and the like; lubricants, such as hydrogenated vegetable oil, sutearic acid, and the like; diluents, such as lactose, mannose, and sucrose; disintegrants, such as carbox.nmethylcellulose and sodium starch glycolate; suspending agents, such as povidone, polyvinyl alcohol, and the like; absorbants, such as silicon dioxide; preservatives, such as methylparaben, propylparaben, and sodium benzoate; surfactants, such as sodium lauryl sulfate, polysorbate 80, and the like; colorants such as F.D. & C. dyes and lakes; flavorants; and sweeteners.

The invention will now be further described by way of the following non-limiting examples.

Example

Delayed-Release Carbohydrate Formulations for Athletic Performance Enhancement

The goal of the Example is to develop a nutrition fluid that delivers carbohydrates and other nutrients to an athlete in a manner that promotes peak athletic performance. The proposed approach is to engineer controlled release of digestible carbohydrates from aqueous dispersion of suitable micro or nanospheres. Important digestible carbohydrates include: the monosaccharides—glucose, fructose and galactose; the disaccharides—sucrose, maltose and lactose; and the polysaccharide, starch. Starch is broken down in to dextrins by salivary amylase (in the mouth) and pancreatic amylase (in the small intestine). Dextrin is acted upon by the brush border enzymes in the small intestine, which also convert the double sugars into simple sugars. The monosaccharides are finally transported across the intestinal epithelium into the bloodstream. The proposed research seeks controlled release of digestible carbohydrates, especially the simple sugars, glucose and fructose, for sustained uptake into the blood.

A basic understanding of the physiology of the gastrointestinal (GI) tract is useful in the design of the delivery system. The retention time of food in the stomach is up to 2 hours and depends, among other factors, on the calorific value of the meal (see, e.g., Hadi, N. A.; Giouvanoudi, A.; Morton, R.; Horton, P. W.; Spyrou, N. M. Variations in gastric emptying times of three stomach regions for simple and complex meals using scintigraphy. *IEEE Transactions on Nuclear Science* 2002, 49, 2328-2331). The controlled release system should be able to withstand the acidic pH (1-3) of the stomach during gastric retention, without releasing the sugar payload. Residence time in the small intestine, where most of the nutrient absorption occurs, is about 3 h. For nutrient delivery over a longer time period, it is necessary to prolong intestinal retention which may be achieved by encapsulating the nutrient in a carrier with mucoadhesive properties. Hydrophilic polymers containing carboxylic acid groups exhibit good mucoadhesive properties. A key step in the design of a controlled release system for sugar is the selection of a carrier material for encapsulating carbohydrates. Polysaccharides and their derivatives are polymers of choice as carriers for sustained-release drug delivery and scaffolds in tissue engineering because of their non-toxic nature and excellent biocompatibility (see, e.g., Dumitriu, S.; Dumitriu, M. Hydrogels as support for drug delivery systems. In *Polysaccharides in Medicinal Applications*; Dumitriu, S. Ed.; Dekker: New York, 1996; pp 705-764; Coviello, T.; Matricardi, P.; Marianecci, C.; Alhaique, F. Polysaccharide hydrogels for modified release formulations. *J. Control. Rel.* 2007, 119, 5-24 and Kong, H.; Mooney, D. J. Polysaccharide-based hydrogels in tissue engineering. In Polysaccharides, $2^{nd}$ ed.; Dumitriu, S., Ed.; Dekker: New York, 2005; pp 817-837). They have also been used for flavor encapsulation in food formulations (see, e.g., Madene, A.; Jacquot, M.; Scher, J.; Desobry, S. Flavour encapsulation and controlled release—a review. *International Journal of Food Science and Technology* 2006, 41, 1-21).

Blends of polysaccharides are used to synthesize aqueous dispersions of micro- or nanoparticles. Hydrophobically modified polysaccharides such as hydroxypropyl cellulose or hydroxyethyl cellulose are known to spontaneously form nanoparticles in water. Interpenetrating polymer networks of these polymers, with polysaccharides containing carboxylic acid groups, are synthesized. FIG. 1 shows the chemical structures of three important carboxy-containing polysaccharides. The monomeric unit of the carboxymethylcellulose backbone consists of D glucose residues linked through $\beta$-(1→4) bonds. Alginates are composed of (1→4)-linked $\beta$-D-mannuronic acid and $\alpha$-L-guluronic acid monomers which vary in amount and sequential distribution along the polymer chain depending on the source of alginate. Hyaluronic acid is a straight polymer consisting of alternating (1→4)-linked 2-acetamide-2-deoxy-$\beta$-D-glucose and (1→3) linked $\beta$-D-glucuronic acid.

To increase stability of the particles in the GI tract, the particles are crosslinked to form hydrogels. Different crosslinking mechanisms are investigated to achieve the desired release kinetics. Crosslinking is performed using free radical initiators such as persulfate salts, or redox systems involving ascorbic acid, or a naturally occurring crosslinker such as genipin. Ionic crosslinking is also explored. Anionic polysaccharides such as gellan can be used for ionic crosslinking, instead of chemicals such as borax which may not be desirable in a food formulation.

It is expected that the carboxy containing hydrogel particles are in a collapsed state in the acidic environment of the stomach. Hence, the encapsulated sugar molecules are retained within the particles in the stomach. The hydrogel particles will achieve an expanded state when they reach the small intestine (pH 5-7), and will release the encapsulated sugar at a rate faster than that in the stomach.

Several researchers have investigated the synthesis of polysaccharide particles and hydrogels for controlled release. Most of these studies were, however, focused on incorporating relatively hydrophobic drugs or protein macromolecules in the carriers. An objective of the proposed research is to encapsulate small hydrophilic molecules such as sugars. The equilibrium partitioning of sugar molecules between the hydrogel particles and the aqueous phase is determined. Due to similarities in the chemical structures of the polysaccharide carrier and the encapsulated monosaccharides, it is expected that the encapsulation efficiency of polysaccharide hydrogels are higher than those of other hydrogels.

There are only a few studies that have reported delayed release systems for carbohydrates. Fox and Allen (Fox, G. J.; Darlene, A. Method and composition for controlling the release of carbohydrates by encapsulation. U.S. Pat. No. 5,536,156, Jul. 16, 1996) have coated carbohydrate microparticles with an edible delayed-release coating. The coated carbohydrate, when orally ingested, causes a time delayed release of the carbohydrate into the digestive system. The coated particles were 30 to 100 µm in size and were stored in solid particulate form. In contrast, Applicants seek to develop controlled release particles that are dispersed in an aqueous medium. Lake and Smith (Lake, M.; Smith, U. Composition and method for long-term glycemic control. Int. Pat. Appl. WO/2006/022585, Feb. 3, 2006) have reported the preparation of starch granules that can be used for improved long-term control of blood glucose in a diabetic patient. The delayed-release starch formulation was designed to reduce the incidence of nocturnal hypoglycemia, wherein the patient would ingest a therapeutic amount of starch granules at bedtime. Zecher (Zecher, D. C. Controlled release carbohydrate embedded in a crosslinked polysaccharide. Int. Pat. Appl. WO/2000/032064, Aug. 6, 2000) has reported a similar controlled release carbohydrate composition consisting of covalently crosslinked polysaccharides. However, the crosslinked carbohydrates were not in a particulate form, and were not in the form of aqueous suspensions.

The following sections will describe methods for the synthesis of polysaccharide hydrogels.

Hydrophobized polysaccharides are highly promising in the synthesis of nanoparticles because of their self-assembling properties in aqueous environment. Akiyoshi and Sunamoto (Akiyoshi, K.; Sunamoto, J. Supramolecular assembly of hydrophobized polysaccharides. *Supramolecular Science* 1996, 3, 157-163) found that polysaccharides that were functionalized with hydrophobes such as cholesterol spontaneously formed nanoparticles when dispersed in water. The size, density and colloidal stability of the nanoparticle could be controlled by tailoring the grafting density and degree of hydrophobicity of the hydrophobe. Polysaccharides such as pullulan, dextran and mannan were partly substituted by various hydrophobic groups such as long alkyl chains and cholesterol. For example, pullulan with a molecular weight of 55 kDa, when functionalized with cholesterol (~1.7 cholesterol moieties per 100 units of glucose) spontaneously formed nanoparticles that were 20-30 nm in size (Akiyoshi, K.; Deguchi, S.; Tajima, H.; Nishikawa, T.; Sunamota, J. Self-assembly of hydrophobized polysaccharide: Structure of hydrogel nanoparticle and complexation with organic compounds. *Proc. Japan Acad.* 1995, 71, 15-19). The cholesterol bearing pullulan self-aggregated to form monodisperse stable nanoparticles after ultrasonification of the suspension in water. No coagulation occurred even after heating at 90° C. for 1 h. These nanoparticles were used for hosting hydrophobic substances such as antitumor adriamycin (Akiyoshi, K.; Taniguchi, I.; Fukui, H.; Sunamoto, J. Hydrogel nanoparticle formed by self-assembly of hydrophobized polysaccharide. Stabilization of adriamycin by complexation. *European Journal of Pharmaceutics and Biopharmaceutics* 1996, 42, 286-290) and various water-soluble proteins, but encapsulation of small water-soluble molecules was not reported.

Simi and Abraham (Simi, C. K.; Abraham, T. E. Hydrophobic grafted and crosslinked starch nanoparticles for drug delivery. *Bioprocess and Biosystems Engineering* 2007, 30, 173-180) have grafted fatty acid on to starch using potassium persulfate as catalyst. Nanoparticles resulting from the modified starch molecules were further stabilized by cross-linking with sodium tripolyphosphate. The nanoparticles were used for encapsulation of a hydrophobic drug.

Thielemans et al. (Thielemans, W.; Belgacem, M. N.; Dufresne, A. Starch nanocrystals with large chain surface modifications. *Langmuir* 2006, 22, 4804-4810) were also successful in surface-modification of nanoscale starch particles using stearic acid chloride (a hydrophobe) and poly(ethylene glycol) methyl ether (a hydrophilic molecule). Woo et al. (Woo, B. H.; Jiang, G.; Jo, Y. W.; DeLuca, P. P. Preparation and characterization of a composite PLGA and poly(acryloyl hydroxyethyl starch) microsphere system for protein delivery. *Pharmaceutical Research* 2001, 18, 1600-1606) have reported the synthesis of polysaccharide microspheres using acryloyl-modified hydroxyethyl starch. The microspheres were investigated for their ability to load protein for controlled protein delivery.

Basheer et al. (Besheer, A.; Hause, G.; Kressler, J.; Mader, K. Hydrophobically modified hydroxyethyl starch: Synthesis, characterization, and aqueous self-assembly into nano-sized polymeric micelles and vesicles. *Biomacromolecules* 2007, 8, 359-367) reacted hydroxyethyl starch with fatty acids (lauric, palmitic, and stearic acids) under mild reaction conditions using dicyclohexyl carbodiimide (DCC) and dimethylaminopyridine (DMAP). The resulting polymers self-assembled to form 20-30 nm micelles and 250-350 nm polymeric vesicles. However, chemicals such as DCC and DMAP are potentially toxic and cannot be used in edible formulations.

Chakraborty et al. (Chakraborty, S.; Sahoo, B.; Teraoka, I.; Gross, R. A. Solution properties of starch nanoparticles in water and DMSO as studied by dynamic light scattering. *Carbohydrate Polymers* 2005, 60, 475-481) have studied the solution properties of starch nanoparticles in water using dynamic light scattering. The nanoparticles were obtained from Ecosynthetix (Lansing, Mich.), and were synthesized from corn starch using glyoxal as crosslinker. A mixture of starch, glycerol (18 wt % of dry starch), and glyoxal (0.1-10 wt %) was extruded to obtain crosslinked starch granules. The granules were cryogenically ground and sieved to obtain particles smaller than 150 nm in diameter. Dynamic light scattering or the particles in water indicated two main populations, with mean diameters of 40 and 300 nm, consisting of isolated starch nanoparticles and their aggregates, respectively. At higher concentration (~3% w/w), a third peak appeared at around 1 μm, because of particle aggregation. Control of particle aggregation is an important step in the design of carbohydrate nanoparticles.

A key feature of the proposed polysaccharide hydrogels is their pH responsiveness. Ideally, the hydrogels should not swell in the acidic environment of the stomach, but should swell upon entry into the small intestine and release the encapsulated sugars at a controlled rate. This section reviews an extreme case where the polysaccharide matrix was insoluble in acidic environments, while it completely dissolved at higher pH values.

Scleroglucan is a branched homopolysaccharide that gives only D-glucose upon complete hydrolysis. The polymer consists of a main chain of $(1\rightarrow 3)$-linked β-D-glucopyranosyl units. At every third unit along the main chain, the polymer bears a single $(1\rightarrow 6)$-linked β-D-glucopyranosyl unit as a branch. The glucopyranose side chain of scleroglucan was oxidized by means of a two-step reaction: first with periodate, to form an aldehyde derivative, and then with chlorite, which resulted in the carboxylated derivative called sclerox (see, e.g., FIG. 2 and Coviello, T.; Palleschi, A.; Grassi, M.; Matricardi, P.; Bocchinfuso, G.; Alhaique, F. Scleroglucan: A versatile polysaccharide for modified drug delivery. *Molecules* 2005, 10, 6-33). By varying the ratio between oxidizing agent and polysaccharide, the polymer could be oxidized to a different extent. It was found that above a 60% oxidation, sclerox became sensitive to environmental conditions giving a reversible sol-gel transition mediated by pH. Permeation of model molecules occurred at different rates through the sol and the gel, and consequently, release from sclerox tablets showed different profiles in the two environments simulating the gastric and the intestinal fluids, respectively.

In acidic medium the formation of a swelled layer around the dosage form acquired a fundamental role in determining the rate of delivery, while at higher pH values erosion and dissolution became predominant. Addition of an acid substance, such as citric acid, in the formulation reduced the release rate in simulated intestinal fluid. The delivery rate was still too rapid in relation to the transit time through the GI tract. Thus another strategy was used. The polysaccharide was first derivatized to introduce aldehydic or carboxylic groups on the side chain. These groups were then cross-linked to produce more stable three-dimensional networks.

Pitarresi et al. have reported crosslinking of methacrylic anhydride functionalized carbohydrates by UV irradiation. Hyaluronic acid was first derivatized with methacrylic anhydride. Relatively low molecular-weight hyaluronic acid (174 kDa) was dissolved in water to form a 2% (w/v) solution. A 20-fold excess of methacrylic acid (with respect to the moles of repeating unit of hyaluronic acid) was added with simultaneous addition of 5 N NaOH (to maintain the pH between 8 and 9). The reaction was kept at 4° C. and stirred for 24 h. The reaction mixture was then precipitated in ethanol and the product was recovered and purified by centrifugation and gel permeation chromatography.

Giezen et al. have disclosed a process for producing biopolymer nanoparticles in which a starch or a starch derivative was crosslinked using dialdehyde or polyaldehyde (see, e.g., Giezen, F. E.; Jongboom, R. O. J.; Fell, J.; Gotlieb, K. F.; Boersma, A. Biopolymer nanoparticles. U.S. Pat. No. 6,677,386, Jan. 13, 2004). A plasticizer, glycerol, was used during the process, along with an acid such as maleic acid, oxalic acid, or citric acid. It should be noted that chemicals such as dialdehydes and glycerol are not suitable as food ingredients. The crosslinked nanoparticles had an average particle size below 400 nm. The viscosity of an aqueous dispersion containing 10 wt % of these particles had a viscosity below 150 mPas (measured at a shear rate of 186 $s^{-1}$).

The formulation viscosity is expected to increase with an increase in particle concentration. As a first approximation, viscosity of a suspension is related to the particle concentration through the Einstein's equation, $\eta=\eta_w(1+2.5\phi)$, where $\eta$ is the viscosity of the dispersion, $\eta_w$ is the viscosity of the aqueous phase, and $\phi$ is the volume fraction of particles in the dispersion. The particle volume fraction is given by $$\phi = \left[1 + \left(\frac{\rho_p}{\rho_w}\right) \cdot \left(\frac{1}{m} - 1\right)\right]^{-1},$$

where $\rho_p$ is the density of the particles, $\rho_w$ is the aqueous phase density, and m is the mass fraction of particles in the dispersion. Dispersion viscosity also depends on the interparticle distance, H, which is the average distance between the surfaces of two neighboring particles in the dispersion. For a population of monodisperse particles with hexagonal close packed structure, the interparticle distance is given by $$H = D\left\{\left(\frac{0.74}{\phi}\right)^{1/3} - 1\right\}$$

where D is the particle diameter. Therefore, for a given mass fraction of polymer in the dispersion (that is, a fixed $\phi$) the dispersion viscosity is expected to be higher when the particles are smaller in size. In this Example, the viscosity of the dispersion is tailored to be close to that of water (~1 mPas).

Magnani et al. have synthesized polysaccharide hydrogels using alginates, hyaluronane, and carboxymethylcellulose (see, e.g., Magnani, A.; Rappuoli, R.; Lamponi, S.; Barbucci, R. Novel polysaccharide hydrogels: characterization and properties. *Polym. Adv. Technol.* 2000, 11, 488-495 and Barbucci, R.; Consumi, M.; Lamponi, S.; Leone, G. Polysaccharides based hydrogels for biological applications. *Macromol. Symp.* 2003, 204, 37-58). The crosslinking procedure consisted of activating the carboxylate moieties by 2-chloro-1-methylpyridinium iodide and using 1,3-diaminopropane as a crosslinker. Aqueous solution of the sodium hyaluronate, alginate and carboxymethyl cellulose were transformed in carboxylic acid by treatment with a strong acid exchange resin Dowex 50 WX8 (Fluka) at 4° C. The solution was added to a 5% tetrabutylammonium hydroxide solution to achieve a pH between 8 and 9. After lyophilization the tetrabutylammonium salt of the polysaccharide was dissolved in dimethylformamide (DMF). A stoichiometric quantity of 2-chloro-1-methylpyridinium iodide was added to the solution kept at 0° C. The crosslinking diamine was then added in excess to the solution and the reaction mixture was maintained under stirring at room temperature for 4 h. The reaction was facilitated by the addition of a small amount of triethylamine, which acted as hydrogen iodide captor. Macroscopic gels were obtained. The synthesis of micro- or nanoparticles was not reported. Moreover, the chemicals involved are not suitable for food formulation.

Kabra et al. prepared macrogels of hydroxylpropyl cellulose by crosslinking the polymer with divinyl sulfone at a temperature above the lower critical solution temperature (LCST, 41° C.) (see, e.g., Kabra, B. G.; Gehrke, S. H.; Spontak, R. J. Microporous, responsive hydroxypropyl cellulose gels. 1. Synthesis and microstructure. *Macromolecules* 1998, 31, 2166-2173). Cai et al. used the same reaction to prepare aqueous suspensions of hydroxylpropyl cellulose nanoparticles (see, e.g., Cai, T.; Hu, Z.; Marquez, M. Synthesis and self-assembly of nearly monodisperse nanoparticles of a naturally occurring polymer. *Langmuir* 2004, 20, 7355-7359). High molecular weight (~$10^6$ Da) was dissolved in an aqueous solution of sodium hydroxide (pH 12). Dodecyltrimethylammonium bormide and dinvyl sulfone were added as the surfactant and crosslinker, respectively. The solution was heated to a temperature above the LCST for about 3 h resulting in nanoparticles with diameters ranging from 170 nm to 430 nm. The particle concentration was below 0.1 wt %. Gao et al. have also reported in situ crosslinking of self-associated hydroxypropyl cellulose nanoparticles using divinyl sulfone (see, e.g., Gao, J.; Haidar, G.; Lu, X.; Hu, Z. Self-association of hydroxypropylcellulose in water. *Macromolecules* 2001, 34, 2242-2247).

De Nooy et al. have used the reaction between a carboxylic acid, an aldehyde, and an isocyanide (the Passerini three-component condensation) to prepare polysaccharide hydrogels (see, e.g., De Nooy, A. E. J.; Masci, G.; Crescenzi, V. Versatile synthesis of polysaccharide hydrogels using the Passerini and Ugi multicomponent condensations. *Macromolecules* 1999, 32, 1318-1320). Carboxylic acid containing carbohydrates such as carboxymethyl cellulose or hyaluronic acid were used to prepare the hydrogels. Polysaccharides such as scleroglucan or pullulan that do not contain carboxylic acid groups were partially oxidized using TEMPO to introduce aldehyde and carboxylic acid groups. The Ugi condensation reaction involves an additional component, an amine. Formaldehyde or glutaraldehyde were used along with amines such as 1,5-diaminopentane or ammonium chloride for the condensation reaction. Chitosan was also used in hydrogel synthesis because of the amine groups present in its structure. All the gels synthesized were macroscopic gels. Micro- or nanoparticle synthesis was not reported. Moreover, aldehydes and isocyanides are generally not considered safe as food ingredients.

Covalently crosslinked hydrogels prepared using other crosslinking reactions have also been reported. Dou et al. have synthesized carboxy-functionalized nanoparticles of dextran, hydropropyl cellulose, and hydroethyl cellulose (see, e.g., Dou, H.; Tang, M.; Yang, W.; Sun, K. One-pot synthesis, characterization, and drug loading of polysaccharide-based nanoparticles with carboxy functional groups. *Colloid Polym. Sci.* 2007, 285, 1043-1047). Their procedure, however, involves the use of chemicals such as nitric acid, acrylic acid, cerium (IV) ammonium nitrate, and N,N'-methylene bisacrylamide, which are unsuitable for food formulation. Yu and Hoffman have reported the synthesis of chemically crosslinked sodium alginate/chondroitin 6-sulfate hydrogels for controlled release of a model cationic protein, lysozyme (see, e.g., Yu, X. J.; Hoffman, A. S. Polysaccharide hydrogels as drug delivery matrixes. Proceedings of the $22^{nd}$ International Symposium on Controlled Release of Bioactive Materials, 1995; Controlled Release Society; pp 352-353). The hydrogel was found to be in a condensed state in divalent cation solutions and in a decondensed state in PBS. Chen et al. have reviewed some polysaccharide hydrogels that were used for nasal delivery of peptides and proteins (see, e.g., Chen, J.; Jo, S.; Park, K. Polysaccharide hydrogels for protein drug delivery. *Carbohydrate Polymers* 1995, 28, 69-76). These hydrogels, which were designed for nasal delivery of insulin, included 45 μm starch microspheres (see, e.g., Illum, L.; Jorgensen, H.; Bisgaard, H.; Krogsgaard, O.; Rossing, N. Bioadhesive microspheres as a potential nasal drug delivery system. *Int. J. Pharm.* 1987, 39, 189-199), epichlorohydrin crosslinked dextran (see, e.g., Edman, P.; Björk, E. Routes of delivery: Case studies: (1) Nasal delivery of peptide drugs. *Adv. Drug Delivery Rev.* 1992, 8, 165-177) and hyaluronic acid ester microspheres (see, e.g., Illum, L.; Farraj, N. F.; Fisher, A. N.; Gill, I.; Miglietta, M.; Benedetti, L. M. Hyaluronic acid ester microspheres as a nasal delivery system for insulin. *J. Control. Rel.* 1994, 29, 133-141). The microspheres of hyaluronic esters were 10 to 100 μm in diameter (see, e.g., Benedetti, L. M.; Topp, E. M.; Stella, V. J. Microspheres of hyaluronic acid esters-Fabrication methods and in vitro hydrocortisone release. *J. Control. Rel.* 1990, 13, 33-41).

Figure 2:
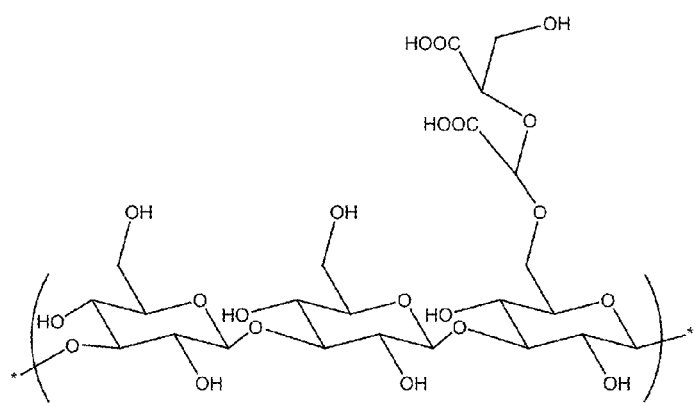
FIG. 2 depicts an oxidized scleroglucan derivative.
Figure 3:
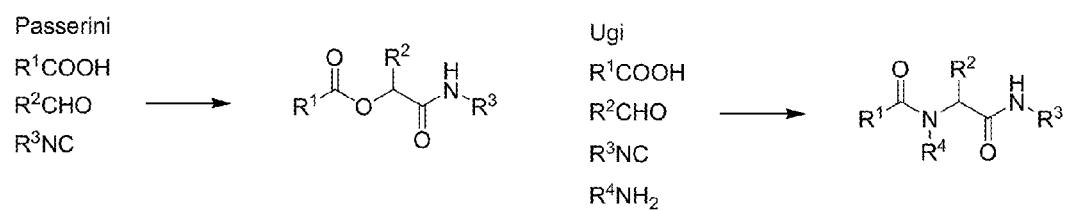
FIG. 3 depicts Passerini and Ugi multicomponent condensation reactions.
Figure 4:
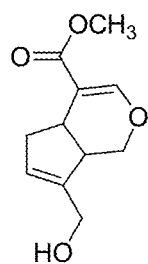
FIG. 4 depicts the structure of genipin.

Selection of a suitable crosslinker is a key step in the preparation of polysaccharide hydrogels for food formulations. Clearly, toxicity of the crosslinking chemical precludes its use. Genipin is a naturally occurring crosslinker for proteins and polysaccharides, and is obtained from gardenia fruit extracts. It has attracted significant interest in the synthesis of polysaccharide hydrogels. It has low acute toxicity ($LD_{50}$ i.v. 382 mg/kg in mice) and is much less toxic than most other chemical crosslinking agents such as glutaraldehyde. Its structure is shown in FIG. 2.

Meena et al. used genipin to crosslink agarose in aqueous medium at pH ~7 at ambient conditions (see, e.g., Meena, R.; Prasad, K.; Siddhanta, A. K. Preparation of genipin-fixed agarose hydrogel. *J. Appl. Polym. Sci.* 2007, 104, 290-296). Genipin was purchased from Challenge Bioproducts Co., Taiwan. The amount of genipin used was about 0.8 wt % of the mass of agarose. Genipin-fixed agarose showed decreased swelling in acidic medium (pH 1.2), representative of the gastric environment. The extent of swelling was 4.8 g/g, whereas the uncrosslinked agarose swelled up to 6 g/g. The authors have reported that, under ambient conditions, maximum crosslinking was achieved after about 85 h.

Alternatively, crosslinking can be achieved using free radicals. Free radical initiators such as ammonium persulfate are listed in GRAS list of chemicals, and can be used in food formulations.

Based on the well known borax mediated crosslinking of polymers containing hydroxyl groups, Palleschi et al. have synthesized hydrogels of scleroglucan using borax (see, e.g., Palleschi, A.; Coviello, T.; Bocchinfuso, G.; Alhaique, F. Investigation of a new scleroglucan/borax hydrogel: structure and drug release. *Int. J. Pharm.* 2006, 322, 13-21). They have studied the release kinetics of model drugs theophylline, vitamin B12 and myoglobin from the crosslinked hydrogels. These hydrogels were macroscopic gels, and not micro- or nanospheres.

Gellan can also be used as an ionic crosslinking agent. Gellan is an anionic microbial polysaccharide that is well known for its gelling properties in the presence of counterions, especially divalent ions, like calcium. Gellan has been used as a crosslinker for scleroglucan.

Figure 5:
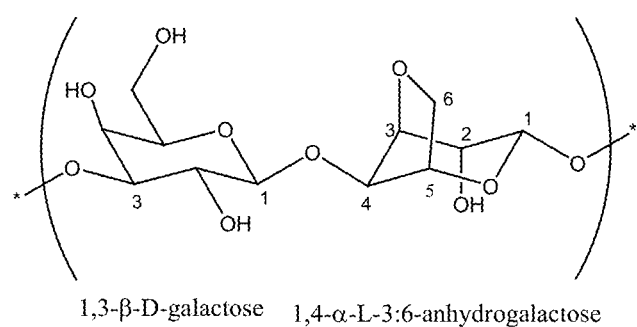
FIG. 5 depicts the structure of carrageenan.
Figure 6:
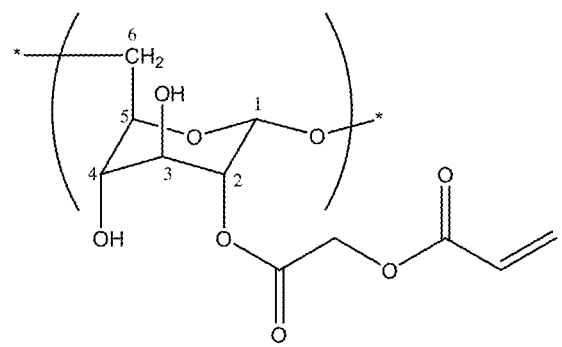
FIG. 6 depicts vinyl-functionalized dextran.

Carrageenans are linear sulfated biopolymers, composed of D-galactose and 3,6-anhydro-D-galactose units. κ-Carrageenan beads are prepared by gelling with monovalent ions (often $K^+$) and sometimes divalent ions. Alginates are linear polysaccharides produced by algae, which contain varying amounts of (1→4)-linked β-D-mannuronic acid and α-L-guluronic acid residues. Mohamadnia et al. have synthesized ionically crosslinked beads of carbohydrate biopolymers κ-carrageenan (FIG. 5) and sodium alginate (see, e.g., Mohamadnia, Z.; Zohuriaan-Mehr, M. J.; Kabiri, K.; Jamshidi, A.; Mobedi, H. pH-Sensitive IPN hydrogel beads of carrageenan-alginate for controlled drug delivery. *J. Bioactive Compat. Polym.* 2007, 22, 342-356 and Mohamadnia, Z.; Zohuriaan-Mehr, M. J.; Kabiri, K.; Jamshidi, A.; Mobedi, H. Ionically crosslinked carrageenan-alginate hydrogel beads. *Journal of Biomaterials Science: Polymer Edition* 2008, 19, 47-59). Alginate gelation takes place when divalent or trivalent cations (usually $Ca^{2+}$) interact ionically with guluronic acid residues, resulting in the formation of a three-dimensional network. Alginate-$Ca^{2+}$ hydrogels have been studied for controlled release oral drug formulations (see, e.g., Bajpai, S. K.; Sharma, S. Investigation of swelling/degradation behavior of alginate beads crosslinked with $Ca^{2+}$ and $Ba^{2+}$ ions. *React. Func. Polym.* 2004, 59, 129-140).

Langer et al. have described the synthesis of interpenetrating polymer networks consisting of ionically or covalently crosslinked hydrogels (see, e.g., Langer, R. S.; Anseth, K.; Elisseeff, J. H.; Sims, D. Semi-interpenetrating or interpenetrating polymer networks for drug delivery and tissue engineering. U.S. Pat. No. 6,224,893, May 1, 2001). Carbohydrates such as hyaluronic acid, dextran, heparin sulfate, chondroitin sulfate, heparin, alginate, gellan and carrageenan were used to synthesize the ionically crosslinked hydrogels. The covalently crosslinked hydrogels consisted of chitosan polymer and isothiocyanate crosslinker. The hydrogels were in the form of viscous solutions capable of retaining biologically active molecules or drugs when injected in vivo. The formation of micro- or nanoparticles was not reported. The use of isothiocyante crosslinker may not be appropriate for food grade hydrogel synthesis.

A blend of hydrophobically modified polysaccharide such as hydropropyl cellulose and a carboxy containing polysaccharide such as alginate or carboxymethyl cellulose is used to prepare the hydrogel particles. The hydrophobically modified polysaccharide results in spontaneous particle formation due to phase separation in water, while the polysaccharide containing carboxylic acid groups imparts a pH-responsive behavior and will also increase intestinal transit time. A review of the formation of hydrogels (both macroscopic gels and aqueous dispersions) using a blend of polysaccharides follows.

Ichikawa et al. have synthesized nanoparticle suspensions of 0.5 wt % concentration by self-assembly of chitosan (with a degree of deacetylation ~77%) and carboxymethyl cellulose hydrolysates (see, e.g., Ichikawa, S.; Iwamoto, S.; Watanabe, J. Formation of biocompatible nanoparticles by self-assembly of enzymatic hydrolysates of chitosan and carboxymethyl cellulose. *Biosci. Biotechnol. Biochem.* 2005, 69, 1637-1642). The polymers were hydrolyzed with the enzymes chitosanase and cellulase, respectively. Electrostatic interactions between the carboxylate groups of carboxymethyl cellulose with the amino groups of chitosan resulted in spontaneous formation of nanoparticles just by mixing solutions of the two polymers. Particle size depended on the mixing ratio of the solutions, and also by the molecular weight of the polymers. It was necessary to hydrolyze the polymers and lower the molecular weight before mixing in order to prevent the formation of macroscopic gel.

Sergio et al. have reported the preparation of hydrogels from mixtures of acidic polysaccharides such as alginates, and basic polysaccharides such as oligosaccharide derivatives of chitosan (see, e.g., Sergio, P.; Ivan, D.; Eleonora, M. Hydrogels of polysaccharide mixtures for tissue engineering and as carriers of active compounds. Int. Pat. Appl. WO/2007/135114, Nov. 29, 2007). They have described the synthesis of microcapsules with a mean diameter of 870 μm using an electrostatic 'bead generator'. An alternative chemical method of synthesizing the particles consisted of, for example, mixing solutions of alginate and lactose derivative of chitosan prepared in 0.15 M NaCl and 10 mM HEPES (pH 7.4). The total polymer concentration was 2% and the weight ratio of polyanion to polycation was 3:1. The particles were typically large in size such that they could be imaged by optical microscopy.

White et al. have prepared hydrogel films (for application in the fields of dermatology, plastic surgery, urology and orthopaedics) using basic polysaccharide such as chitosan and anionic polysaccharide such as hyaluronic acid (see, e.g., White, B. J.; Rodden, G. I. Compositions of semi-interpenetrating polymer network. Int. Pat. Appl. WO/2005/061611, Jul. 7, 2005).

Vieira et al. have prepared hydrogels of oxidized alginate and oxidized alginate blended with chitosan, and studied the interaction of these drugs with the antifolate drug pyrimethamine (see, e.g., Vieira, E. F. S.; Cestari, A. R.; Airoldi, C.; Loh, W. Polysaccharide-based hydrogels: Preparation, characterization and drug interaction behavior. *Biomacromolecules* 2008, 9, 1195-1199). Sodium alginate was partially oxidized using sodium periodate to obtain 2,3-dialdehyde alginate. The periodate was completely removed by extensive dialysis. Gelation of 2,3-dialdehyde alginate was achieved with $CaCl_2$ or chitosan/$CaCl_2$ in the presence of borax. The synthesis of micro- or nanoparticles is not reported.

Meena et al. have discussed the synthesis of a hydrogel system based on grafting of agar and sodium alginate blend with acrylamide (see, e.g., Meena, R.; Chhatbar, M.; Prasad, K.; Siddhanta, A. K. Development of a robust hydrogel system based on agar and sodium alginate blend. *Polym. Int.* 2008, 57, 329-336). Agar and sodium alginate were dissolved separately in distilled water. Agar was dissolved using microwave irradiation at 90° C. for 2 min, while the sodium alginate was dissolved at ambient temperature. Blends of agar and sodium alginate were prepared by mixing agar them in different ratios. The resulting blends were cooled, forming gels which were cut into small pieces and dehydrated with isopropanol. Dewatered, hardened gel particles were filtered through a nylon cloth under reduced pressure and dried in air, followed by drying in an oven at 50° C. for 2 h. The dried blend samples were ground using a mortar and pestle to obtain 20-40 mesh particles.

Hydrogels consisting of a gellan co-crosslinked with scleroglucan have also been reported (see, e.g., Alhaique, F.; Coviello, T.; Rambone, G.; Carafa, M.; Murtas, E.; Riccieri, F. M.; Dentini, M.; Desideri, P. A gellan-scleroglucan co-crosslinked hydrogel for controlled drug delivery. Proceedings of the International Symposium on Controlled Release of Bioactive Materials 1998, 25$^{th}$ 866-867). The use of both gellan and scleroglucan in the hydrogel resulting in better stiffness and stability of the macroscopic hydrogel, and resulted in a slower release of the guest molecule. The release rate was undesirably high from the $Ca^{2+}$ crosslinked gellan alone.

Kim et al. have synthesized polysaccharide-based hydrogel using photocrosslinking of modified dextran (see, e.g., Kim, S. H.; Won, C. Y.; Chu, C. C. Synthesis and characterization of dextran-based hydrogel prepared by photocrosslinking *Carbohydrate Polymers* 1999, 40, 183-190). Dextran contains (1→6)-linked α-D-glucopyranosyl residues, and three hydroxyl groups per glucose residue in the structure. Dextran was first reacted with bromoacetyl bromide. The bormoacetylated dextran was then reacted with sodium acrylate for incorporating vinyl groups. Photocrosslinking was achieved by irradiating the acrylated dextran by UV light. These were macroscopic gels, and not micro- or nanoparticles.

Figure 7:
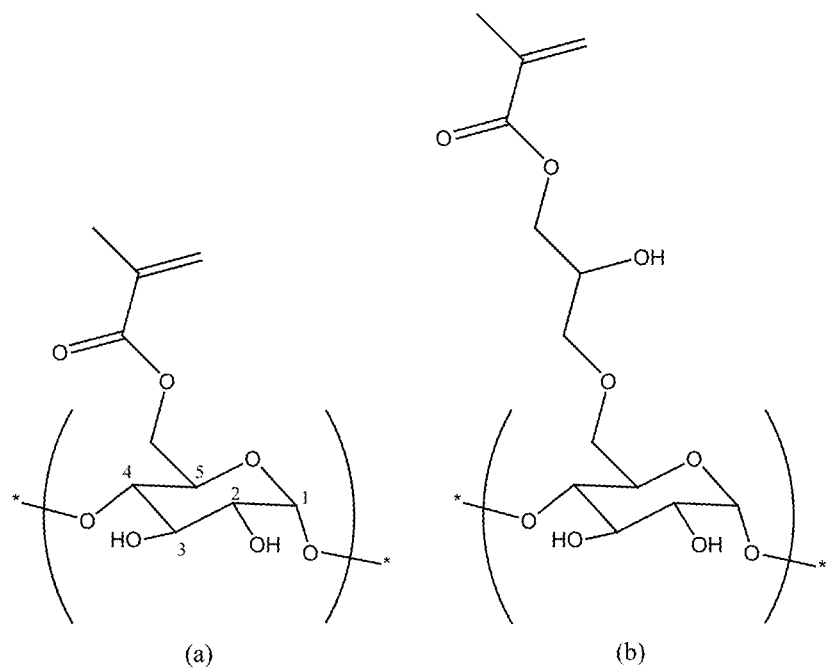
FIG. 7 depicts glycidyl methacrylate adduct of starch resulting from (a) transesterification, and (b) ring opening of the epoxy group.

Similarly, Reis et al. introduced pendent vinyl groups by reacting starch with glycidyl methacrylate (see, e.g., Reis, A. V.; Guilherme, M. R.; Moia, T. A.; Mattoso, L. H. C.; Muniz, E. C.; Tambourgi, E. B. Synthesis and characterization of starch-modified hydrogel as potential carrier for drug delivery system. *J. Polym. Sci.: Part A: Polym. Chem.* 2008, 46, 2567-2574). Starch is a polysaccharide composed of two structural components: amylase and amylopectin. Amylase is a linear chain consisting of 250-300 (1→4)-linked α-D-glucose residues. Amylopectin is a branched molecule consisting of about 1400 D-glucose residues with α(1→4) and α(1→6) linkages. It constitutes about 80% of the total starch and can be easily hydrolyzed. Crosslinkable vinyl groups were introduced by the reaction of starch with glycidyl methacrylate resulting in structures schematically shown in FIG. 7.

Chen et al. synthesized polymerizable saccharide monomers, such as sucrose, by reaction of the sugar with epoxy acrylate, or methacryloyl chloride and acetyl chloride, and used these monomers to form hydrogels (see, e.g., Chen, J.; Bongjo, S.; Park, K. Hydrophilic, hydrophobic, and thermoreversible saccharide gels and foams, and methods for producing same. U.S. Pat. No. 6,018,033, Jan. 25, 2000). Cai et al. have similarly modified hydropropylcellulose by covalently attaching vinyl groups that allowed chemical linking of the polysaccharide chains into nanoparticles through a free radical polymerization process (see, e.g., Cai, T.; Hu, Z.; Ponder, B.; St. John, J.; Moro, D. Synthesis and study of and controlled release from nanoparticles and their networks based on functionalized hydroxypropylcellulose. *Macromolecules* 2003, 36, 6559-6564).

As mentioned previously, reports on encapsulation of hydrophilic molecules in particulate carriers of aqueous dispersions are not numerous. Edlund and Albertsson varied the crosslink density of hemicellulose-based hydrogel microspheres and found that the crosslinked network was not able to retard the rapid release of the small and hydrophilic molecules of compounds such caffeine (see, e.g., Edlund, U.; Albertsson, A.-C. A microspheric system: hemicellulose-based hydrogels. *Journal of Bioactive and Biocompatible Polymers* 2008, 23, 171-186). On the contrary, release of a macromolecule such as protein (bovine serum albumin) could be controlled by varying the network mesh size, with the release proceeded by Fickian diffusion. Other studies have shown the same dependence of size and hydrophilicity of entrapped molecules.

Figure 10:
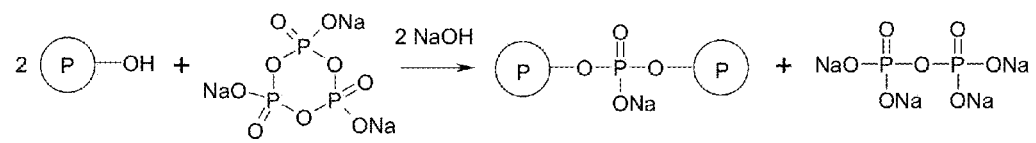
FIG. 10 depicts crosslinking of hydroxyl containing polysaccharides using TSTMP in the presence of sodium hydroxide.

Applicants synthesized hydroxypropyl cellulose microgels using relatively non-toxic crosslinking agents such as trisodium trimetaphosphate (TSTMP) and sodium tripolyphosphate (STPP). Hydroxypropyl cellulose (HPC) is prepared by base-catalyzed reaction of propylene oxide with cellulose. HPC is permitted in foods for human consumption, and is described under section 121.1160 of the U.S. Food and Drug Administration regulations [Klug, E. D. Hydroxypropyl Cellulose. In *Encyclopedia of Polymer Science and Technology*; Bikales, N. M., Ed.; Wiley Interscience: New York, 1971; Vol. 15, pp 307-314]. Up to 0.4 wt % of unreacted TSTMP and STPP are permissible in food products according to FDA regulations. Other reagents permitted by FDA for making food grade starch, such as phosphoryl chloride, adipate, and adipic-acetic mixed anhydride, may also be used for the crosslinking reaction. Carcinogens such as epichlorohydrin, although used in the past for crosslinking starch, can obviously not be used. See, e.g., FIG. 10 which depicts crosslinking of hydroxyl containing polysaccharides using TSTMP in the presence of sodium hydroxide.

Crosslinking of starch using trisodium trimetaphosphate has been typically carried out in aqueous media at pH of 11.5 [Xie, S. X.; Liu, Q.; Cui, S. W. *Starch modification and application*. In Food Carbohydrates: Chemistry, Physical Properties, and Applications; Cui, S. W. Ed.; Taylor & Francis: New York 2005; p. 358]. The reaction is allowed to proceed at 40° C. for 2 to 6 h. The applicants found that hydroxypropyl cellulose microparticles could be obtained, at relatively high concentrations (up to 10 wt %, without macrophase separation), using significantly higher sodium hydroxide concentration and reaction temperature. Sodium hydroxide not only participates in the crosslinking reaction, but also, evidently, lowers the LCST of hydroxypropyl cellulose resulting in particle formation even at room temperature (at sufficiently high concentrations of NaOH).

Hydroxypropyl cellulose powder, obtained from Sigma-Aldrich, was used for microparticle synthesis. The HPC polymer had a number-average molecular weight, $\overline{M}_n$, of 10,000 g/mol, a weight-average molecular weight, $\overline{M}_w$, of 80,000 g/mol, a degree of substitution, DS, of 2.5, and a molar substitution, MS, of 3.7. The degree of substitution, DS, is defined as the average number of hydroxyl groups substituted per anhydroglucose unit [Klug, E. D. Hydroxypropyl Cellulose. *In Encyclopedia of Polymer Science and Technology*; Bikales, N. M., Ed.; Wiley Interscience: New York, 1971; Vol. 15, pp 307-314]. The molar substitution, MS, is defined as the average number of propylene oxide molecules combined per anhydroglucose unit.

About 15 mg of refined soy lecithin (MP Biomedicals) was dissolved in 5 mL of a sodium hydroxide solution (pH=12) to obtain a pale yellow translucent solution. Four hundred milligram of HPC was added to this solution and stirred to result in a viscous solution. In another vial, a 12% (w/v) solution of TSTMP was prepared in distilled water. Five milliliters of this TSTMP solution was then added to the HPC/soy lecithin solution. The mixture was stirred to obtain a homogeneous solution, which was heated at 50° C. for 1 h and subsequently cooled to room temperature. The pH of the resulting dispersion, measured using a stainless steel ISFET pH probe (IQ Scientific Instrument), was 7.8. The pH was adjusted to 7 using a few microliters of 4 M hydrochloric acid. The HPC dispersion consisted of: 400 mg of HPC (3.2 mmol of hydroxyl groups), 15 mg (0.05 mmol) soy lecithin, 600 mg (2.0 mmol) of TSTMP, and about 12 mg (0.3 mmol) sodium hydroxide in about 10 mL of distilled water. The number-average particle diameter was 3.5 µm and the weight-average particle diameter was 3.7 µm. The viscosity of the dispersion was about 11 cP. Ten milliliters of a 20% (w/v) dextrose solution in distilled water was then added to this dispersion, and the mixture was heated at 60° C. for 10 min. The number-average particle diameter remained nearly the same (~5 µm) after addition of dextrose. The viscosity of the final dispersion was about 5 cP. The average diameter of the particles in the dispersion was determined using a ALVS-NIBS High Performance Particle Sizer (ALV-GmbH, Langen/Germany). Dispersion viscosity was determined using a Ubbelohde Viscometer (Cannon Instrument Co., Pennsylvania).

There were no significant differences in the particle sizes or the dispersion viscosities when the formulations were heated at 50° C. for 3 h instead of 1 h.

In another formulation, 10 mL of a 4% (w/v) solution of HPC in distilled water was taken in a glass vial. Sodium hydroxide pellets (310 mg, 7.75 mmol) were added and dissolved in to this solution. The addition of sodium hydroxide resulted in a cloudy homogeneous dispersion. TSTMP (600 mg, 1.96 mmol) and soy lecithin (14 mg, 0.043 mmol) were subsequently added and dissolved. The dispersion was heated at 50° C. for 1 h, after which it was cooled to room temperature. The procedure resulted in the formation of macroparticles that settled to the bottom of the vial. Immediately after cooling, the dispersion was stirred (using a magnetic stirrer) and neutralized to pH 7 using 4 M hydrochloric acid. The number- and weight-average particle diameters in the supernatant phase were about 610 nm and 690 nm, respectively. The viscosity of the HPC dispersion was about 1.6 cP. Ten milliliters of a 20% (w/v) dextrose solution in distilled water was then added to this dispersion, and the mixture was heated at 60° C. for 10 min. The number-average particle diameter in the dextrose loaded dispersion was about 1.6 µm and the weight-average particle diameter was about 2.2 µm after addition of dextrose. The viscosity of the final dispersion was about 2 cP.

In another embodiment, heating a solution of 4 g of HPC (31.9 mmol of hydroxyl groups) in 100 g of water with 2.1 g (52.5 mmol) of sodium hydroxide and 1 g (3.27 mmol) of TSTMP at 110° C. for 2 h, resulted in the formation of hydrogel microspheres. The dispersion was cooled to room temperature and neutralized using about 4 mL of 4 M hydrochloric acid to result in a solution with a viscosity of about 22 cP and a weight-average particle diameter of about 3.4 µm. Addition of 104 mL of 20% (w/v) dextrose solution gave a final dispersion with a sugar concentration of 10% (w/v), a viscosity of 6.8 cP and a weight-average particle diameter of about 4.1 µm. The formulation was heated at 60° C. for 10 min after the addition of sugar solution.

In another formulation, 8 g of HPC (63.7 mmol of hydroxyl groups) dissolved in 100 g of water was heated with 2.23 g (55.8 mmol) of sodium hydroxide and 1 g (3.27 mmol) of TSTMP. Heating was carried out in a sealed glass reactor at 110° C. for 2 h. After cooling, the unreacted sodium hydroxide was neutralized using about 20 mL of 4 M hydrochloric acid, to yield a dispersion of crosslinked HPC microspheres with a weight-average particle diameter of about 4.3 µm. The viscosity of the dispersion was about 31.2 cP. A 20% (w/v) dextrose solution (120 mL) was then added to obtain a formulation with 10% (w/v) dextrose, 3.3% (w/v) HPC, about 2.5% (w/v) sodium chloride. The dispersion was heated at 60° C. for 10 min after sugar addition. The weight-average particle diameter in the final dispersion was about 4.5 µm, and the dispersion viscosity was about 31 cP. The dispersion viscosity was sensitive to the order in which the solutions were mixed. If the dextrose solution was added after the second heating step (60° C. for 10 min), the viscosity of the resulting dispersion was higher (about 55 cP).

Microparticle hydrogels of hydroxypropyl cellulose and sodium alginate (CAS no. 9005-38-3; American International Chemical, Inc., F-200) are synthesized as follows. Ten milligrams of HPC (0.080 mmol of hydroxyl groups) was dissolved in 1 mL of distilled water. To this solution was added 1 mL of 2.5 M NaOH solution (2.5 mmol NaOH), 20 mg (0.065 mmol) of trisodium trimetaphosphate, 10 mg of sodium alginate and 2 mg (6.1 µmol) of soy lecithin. The solution was stirred thoroughly. A cloudy dispersion was obtained that remained stable even after adding a few drops of concentrated hydrochloric acid (leading to a final pH of about 2, simulating the acidic environment of the stomach).

Hydroxypropyl cellulose self-assembles in water at a temperature greater than 41° C. This temperature, above which spontaneous self-assembly of the polymer chain occurs, is called the lower critical solution temperature (LCST). Thermal self-assembly of HPC is a reversible process. Individual polymer chains constituting the microparticles get solvated by water molecules when the solution is cooled below the LCST. Crosslinking the HPC chains using trisodium metaphosphate (TSTMP) prevents dissolution of the microparticles when the solutions are cooled below the critical solution temperatures.

Figure 11:
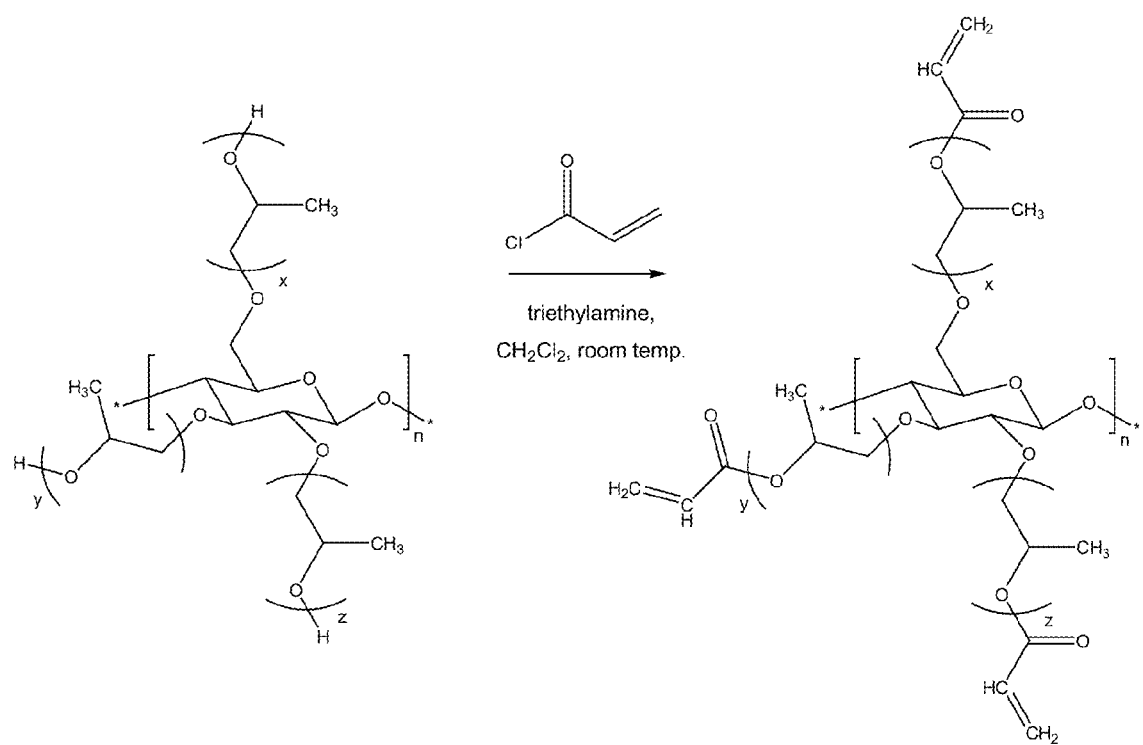
FIG. 11 depicts synthesis of acrylated hydroxypropyl cellulose.

In another strategy, crosslinking may be achieved by functionalizing the polysaccharide using acryloyl (or methacryloyl) groups using acryloyl chloride (or methacryloyl chloride). Formation of acryloyl esters results from the reaction of acryloyl chloride with the hydroxyl groups of the polysaccharide (FIG. 11). It is important, however, to completely remove unreacted acryloyl chloride from the functionalized polymer, because of toxicity of acryloyl chloride. The vinyl functionalized HPC may then be crosslinked in water, above the LCST, using a relatively benign free-radical redox-initiator such as ascorbic acid and hydrogen peroxide, or thermal initiator such as potassium persulfate.

Thus, 1 g of hydroxypropyl cellulose (8 mmol) was taken in a round bottom flask equipped with a magnetic stir bar and fitted with a rubber septum. The polymer was dissolved in 20 mL of anhydrous dichloromethane to obtain a cloudy, viscous solution. The air in the flask was purged with dry nitrogen. About 1 mL (7 mmol) of triethyl amine was injected in to the reactor, followed by drop-wise addition of about 520 µL (6.4 mmol) of acryloyl chloride. The mixture was stirred at room temperature, whereupon the cloudy solution became clear few minutes after the addition of acryloyl chloride. The solution was stirred overnight, after which the acrylated hydroxypropyl cellulose product was recovered and purified by repeated precipitations in cold (~0° C.) diethyl ether and acetone. The product was dried in vacuo at 40° C. About 40 mg of the acrylated HPC polymer was dissolved in 2 mL distilled water to obtain a cloudy solution at room temperature. About 65 mg (200 mmol) of soy lecithin was added to this solution and dissolved. The solution of HPC and soy lecithin was de-oxygenated by bubbling nitrogen gas, after which a 2 mL of a degassed solution of ammonium persulfate (9.1 mg, 40 mmol) was injected. The solution was heated at 70° C. for 2 h to obtain a dispersion of crosslinked acrylated hydroxypropyl cellulose particles. The number-average and weight-average particle diameters were 1.28 µm and 1.34 µm, respectively.

In an emulsion-based synthesis of hydroxypropyl cellulose microgels, 80 mg of acrylated hydroxypropyl cellulose was dissolved in 2 mL of dichloromethane. Distilled water (4 mL) was added to this solution and stirred to obtain an emulsion. Crosslinking of the acrylated hydroxypropyl cellulose was carried out at 35° C. using a redox system of ammonium persulfate and dextrose. Dextrose (21.6 mg, 12 mmol) was dissolved in the emulsion. Two milliliters of a solution of ammonium persulfate (27.4 mg, 0.12 mmol) in distilled water (2 mL) was injected in to the emulsion to initiate the crosslinking reaction. Dichloromethane was removed from the resulting dispersion using a rotary evaporator. A cloudy dispersion of crosslinked acrylated hydroxypropyl cellulose microgels was obtained. The crosslinked particles settled to the bottom of the vial on standing, and could therefore be isolated in a powder form by decanting the supernatant. The crosslinking may also be carried out using redox systems such as persulfate/glucose, hydrogen peroxide/ascorbic acid, etc.

Scanning electron microscopy of a 400 mg HPC, 100 mg TSTMP, 200 mg NaOH, 10 mL water solution heated at 110° C. for 2 h, wherein the dispersion was neutralized with concentrated HCl acid revealed large (~1 µm) cubic particles seen under SEM. HPC has a low glass transition temperature and readily forms a film on the SEM substrate at room temperature. However, it was difficult to image the nanoparticles using SEM.

Having thus described in detail preferred embodiments of the present invention, it is to be understood that the invention defined by the above paragraphs is not to be limited by particular details set forth in the above description as many apparent variations thereof are possible without departing from the spirit or scope of the present invention.

What is claimed is:

1. A hydrogel particle, wherein the particle has a diameter less than or equal to about 1000 micrometers, and wherein the particle comprises:
   (a) at least one biologically active agent;
   (b) one or more compounds for time controlled and sustained release of the at least one biologically active agent of (a) in vivo, wherein the one or more compounds for time controlled and sustained release are non-toxic and are crosslinked;
   (c) at least one compound that is pH-sensitive, wherein the at least one pH-sensitive compound does not swell at pH 1-3; and
   (d) at least one compound that is temperature-sensitive, wherein the at least one temperature-sensitive compound has a lower critical solution temperature in aqueous solution.

2. The hydro gel particle of claim 1, wherein the at least one biologically active agent is a nutritional supplement selected from the group consisting of: minerals, proteins, carbohydrates, amino acids, lipids, electrolytes and vitamins.

3. The hydrogel particle of claim 1, wherein the one or more compounds for the time controlled and sustained release of the at least one biologically active agent are selected from the group consisting of: biodegradable polymers, bioadhesives, and binders.

4. The hydrogel particle of claim 3, wherein the biodegradable polymers and binders are selected from the group consisting of: poly(lactide)s, poly(glycolide)s, poly(lactide-co-glycolide)s, poly(lactic acid)s, poly(glycolic acid)s, poly (lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and polyorthoester, biodegradable polyurethanes, polysaccharides, and polysaccharide copolymers with polyethers.

5. A beverage, a gum, a food snack or a powder comprising a plurality of hydrogel particles of claim 1.

6. The hydrogel particle of claim 1, wherein the hydrogel particle comprises at least one modified polysaccharide.

7. The hydrogel particle of claim 6 wherein the polysaccharide modification is selected from the group consisting of: carboxylic acid, acryloyl or methacryloyl, hydroxyalkyl, ester, grafted fatty acid moieties, oligo(alkylene oxide) grafts, functionalized hydrophobes, grafted amphiphiles, and side chain derivatizations to introduce aldehydic or carboxylic groups.

8. The hydrogel particle of claim 1, wherein the hydrogel particle increases the retention time of the at least one biologically active agent in the small intestine because of the mucoadhesive nature of the hydrogel particle.

9. The hydrogel particle of claim 1, wherein the one or more compounds for time controlled and sustained release are crosslinked using inorganic salts, or free radical initiators, or redox systems involving ascorbic acid, or a naturally occurring crosslinker.

10. The hydrogel particle of claim 9, wherein the one or more compounds for time controlled and sustained release are ionically crosslinked.

11. The hydrogel particle of claim 1, wherein the one or more compounds for time controlled and sustained release are covalently crosslinked.

12. The hydrogel particle of claim 1, further comprising a surfactant.

13. The hydrogel particle of claim 1, wherein the one or more compounds for time controlled and sustained release comprise a polysaccharide, wherein the polysaccharide is a naturally occurring anionic polymer.

14. The hydrogel particle of claim 1, wherein the at least one pH-sensitive compound of (c) is a carboxy-containing polysaccharide.

15. The hydrogel particle of claim 14, wherein the carboxy-containing polysaccharide is alginate or carboxymethyl cellulose.

16. The hydrogel particle of claim 1, wherein the at least one temperature-sensitive compound of (d) is a hydrophobically modified polysaccharide.

17. The hydrogel particle of claim 16, wherein the hydrophobically modified polysaccharide is selected from the group consisting of: hydroxypropyl cellulose, hydroxypropylmethyl cellulose, and hydroxyethyl cellulose.

18. The hydrogel particle of claim 1, wherein the at least one pH-sensitive compound of (c) is a carboxy-containing polysaccharide and the at least one temperature-sensitive compound of (d) is a hydrophobically modified polysaccharide.

19. The hydrogel particle of claim 1, wherein the particle swells in the pH environment of the small intestine.

* * * * *